(12) United States Patent
Okuzawa

(10) Patent No.: US 7,245,749 B2
(45) Date of Patent: Jul. 17, 2007

(54) IMAGE ACQUIRING DISPLAY APPARATUS, METHOD AND APPARATUS FOR EDITING PHOTOGRAPHING CONDITIONS, AND PROGRAM FOR ARRANGING PHOTOGRAPHING CONDITIONS

(75) Inventor: Jiro Okuzawa, Hino (JP)

(73) Assignee: Konica Corporation, Tokyo (JP)

( * ) Notice: Subject to any disclaimer, the term of this patent is extended or adjusted under 35 U.S.C. 154(b) by 967 days.

(21) Appl. No.: 10/349,911

(22) Filed: Jan. 24, 2003

(65) Prior Publication Data

US 2003/0142859 A1 Jul. 31, 2003

(30) Foreign Application Priority Data

Jan. 28, 2002 (JP) ............................. 2002-018404

(51) Int. Cl.
*G06K 9/00* (2006.01)
(52) U.S. Cl. ..................................... 382/128
(58) Field of Classification Search ................ 382/128; 345/418
See application file for complete search history.

(56) References Cited

U.S. PATENT DOCUMENTS

| | | | |
|---|---|---|---|
| 3,859,527 A | 1/1975 | Luckey | |
| 5,636,259 A | 6/1997 | Khutoryansky et al. | |
| 6,275,562 B1 | 8/2001 | He et al. | |
| 6,603,494 B1 * | 8/2003 | Banks et al. ................. | 715/807 |
| 6,714,623 B2 * | 3/2004 | Sako et al. ................. | 378/98.8 |

FOREIGN PATENT DOCUMENTS

| | | |
|---|---|---|
| EP | 0 609 500 A | 8/1994 |
| JP | 55-12144 | 1/1980 |
| JP | 04346124 | * 12/1991 |

OTHER PUBLICATIONS

Robb, R., et al., "Analyze: A Software System for Biomedical Image Analysis", Visualization in Biomedical Computing, 1990, proceedings of the first conference on Atlanta, GA, USA May 22-25, 1990, Los Alamitos, CA, IEEE Comput. Soc., May 22, 1990, pp. 507-518, XP010019055.

* cited by examiner

*Primary Examiner*—Matthew C. Bella
*Assistant Examiner*—Tom Y. Lu
(74) *Attorney, Agent, or Firm*—Finnegan, Henderson, Farabow, Garrett & Dunner, L.L.P.

(57) ABSTRACT

An image acquiring display apparatus comprising an editing system for photographing conditions, a method of editing photographing conditions by using the apparatus, and a program for arranging photographing conditions, in order to select any of photographing conditions rapidly and certainly. The image acquiring display apparatus has: a display for displaying at least a selection screen for selecting a photographing condition required for a patient from a plurality of photographing conditions, and a display screen for displaying image data read out of a radiographic image conversion medium having a radiographic image of the patient, recorded thereon; and an editing section for editing a plurality of photographing conditions to be displayed on the selection screen, of predetermined master data including a plurality of photographing conditions.

13 Claims, 18 Drawing Sheets

FIG.4

| Time | Patient ID | Patient Name | Sex | Age | Department | Location | Photographing Condition | Sheets (Total) |
|------|-----------|--------------|------|-----|------------|----------|------------------------|----------------|
| 12:31 | 1234567890 | Taro KONICA | male | 31 | medicine | new building 2F | chest-A →P | 5 |
| | | | | | | | | |
| | | | | | | | | |
| | | | | | | | | |
| | | | | | | | | |

Schedule=xx Suspend=xx

◀ ◁ ▷ ▶

[Delete] [List Update] [Cancel] [OK]

Determined Photographing Conditions — 15a

- Abdomen-Supine PA
  R ■ 301003201000110000
- Abdomen-Supine LAT
  R ■ 301003201000130000

Previous Page
Next Page
Delete

— 15b

| Favorite | Erect | Supine | | Cassette | |
|---|---|---|---|---|---|
| Large Classification | Head | Neck | Chest | Abdomen | Spine |
| Group 1 | | | | Supine PA | |
| Group 2 | | | | Supine AP | |
| Group 3 | | | | Supine LAT | |
| Group 4 | | | | Supine DEC | |

Previous Page
Next Page
Cancel
OK

Schedule 15c
15

FIG 5D

Determined Photographing Conditions

- Abdomen-Supine AP  R: 10100430100110000
- Abdomen-Supine LAT  R: 10100430100130000

| Favorite | Erect | Supine | Cassette | | |
|---|---|---|---|---|---|
| Large Classification | Head | Neck | Chest | Abdomen | Spine |
| Group 1 | | | | Supine PA | |
| Group 2 | | | | Supine AP | |
| Group 3 | | | | Supine KUB | |
| Group 4 | | | | Decub | |

Previous Page
Next Page
Delete

Previous Page
Next Page
Cancel
OK

Schedule

FIG. 9

| | | Master Name | Extracting Condition | To | | Specify Master | Extracting Condition | | |
|---|---|---|---|---|---|---|---|---|---|
| From | | Maker Master | Head ▼ | | | User Master 1 | Head ▼ | | |

19c — To
19e — Rearrange
19f — Select All

Left table (19a):

| Serial No. | Name |
|---|---|
| 1010010010001... | Skull AP |
| 1010010010001... | Skull PA |
| 1010010010001... | Skull LAT |
| 1010010010001... | Skull RL |
| 1010010010001... | Skull L-LAT |
| 1010010010001... | Skull Oblique |
| 1010010010001... | Skull Towne |
| 1010010010003... | Skull Axial |
| 1010010010003... | Skull Waters |
| 1010010020001... | Sella Frontal |
| 1010010020001... | Sella AP |
| 1010010020001... | Sella PA |
| 1010010020001... | Sella LAT |
| 1010010020001... | Sella RL |
| 1010010020001... | Sella L-LAT |
| 1010010020003... | Sella Towne |
| 1010010030001... | Sinuses Frontal |
| 1010010030001... | Sinuses AP |

Right table (19b):

| Serial No. | Name |
|---|---|
| 1010010010001... | Skull AP |
| 1010010010001... | Skull PA |
| 1010010010001... | Skull LAT |
| 1010010010003... | Skull Towne |
| 1010010010003... | Skull Axial |
| 1010010020001... | Sella AP |
| 1010010020001... | Sella LAT |
| 1010010030001... | Sinuses PA |
| 1010010030001... | Sinuses LAT |
| 1010010030003... | Sinuses Waters |
| 1010010030003... | Sinuses Caldwell |
| 1010010040003... | Tempor... Schuller |
| 1010010040003... | Tempor... Stenvers |
| 1010010040004... | Tempor... Law |
| 1010010040004... | Tempor... IAC |
| 1010010070004... | OpticF... Rhese |
| 1010010100001... | Masal... LAT |
| 1010010100002... | Masal... Axial |

19g — Copy All

19e — Rearrange
19f — Select All
19d — Search
19d — Copy / Search

To Condition key editing screen

FIG.10

Specify Master: User Master 1
Extracting Condition: Head ▼

| Serial No. | Name |
|---|---|
| 101001001001... | Skull AP |
| 101001001001... | Skull PA |
| 101001001001... | Skull LAT |
| 101001001003... | Skull Towne |
| 101001001003... | Skull Axial |
| 101001002001... | Sella AP |
| 101001002001... | Sella LAT |
| 101001003001... | Sinuses PA |
| 101001003001... | Sinuses LAT |
| 101001003003... | Sinuses Waters |
| 101001003003... | Sinuses Caldwell |
| 101001004003... | Tempor... Schuller |
| 101001004003... | Tempor... Stenvers |
| 101001004004... | Tempor... Law |
| 101001004004... | Tempor... IAC |
| 101001007004... | OpticF... Rhese |
| 101001010001... | Masal ... LAT |
| 101001010002... | Masal ... Axial |

[Copy] [Cancel] [Search]

[To Master editing screen]

Favorite — 20b

20c — Head | Neck | Chest | Abdomen | Spine | Thorax
Arm | Leg

Input Condition
Reading Device [ ]

*Primary Condition*
Resolution [High ▼]
Pixel Size [Fine ▼]

*Read Pixel Size*
Size [10"x12" ▼]
Orientation [Portrait ▼]
Position [Middle ▼]

21a

Output Condition
Output Device [ ▼]

*Print Format*
| | A | AB | A/B |
|---|---|---|---|
| 1on1 | | | |
| 2on1 | | AB | A/B |

*Print Format*
Image Size  Output Film
8"x10" → [ ▼]
10"x12" → [ ▼]
11"x14" → [ ▼]
14"x17" → [ ▼]

*Output Method*
[Actual ▼]

*Image Enhance*
Main [ ] [ ▼] [ ] [ ▼]
Sub [ ] [ ▼] [ ] [ ▼]

*Overlay*
Stamp [ ▼] [ ▼] [ ▼] [ ▼]
Right-Left Maker [ ▼] [ ▼] [ ▼] [ ▼]
Orientation Maker
Scale/Grid

[grid preview]

| Condition Key Number | Large Classification Name | Group Name | Condition Key Name | Reading Condition 1 | Reading Condition 2 | Reading Condition 3 | Reading Condition 4 | Reading Condition 5 | Reading Condition 6 | Reading Condition 7 |
|---|---|---|---|---|---|---|---|---|---|---|
| 1 | Head | Skull | A-P | 2 | 2 | 0 | 4 | 1 | 1750 | 0 |
| 2 | Head | Skull | P-A | 2 | 2 | 0 | 4 | 1 | 1750 | 0 |
| 3 | Head | Skull | R-L | 2 | 2 | 0 | 4 | 1 | 1750 | 0 |
| 4 | Head | Skull | L-R | 2 | 2 | 0 | 4 | 1 | 1750 | 0 |
| 5 | Head | Skull | | 1 | 0 | 0 | 4 | 1 | 1750 | 0 |
| 6 | Head | Skull | | 1 | 0 | 0 | 4 | 1 | 1750 | 0 |
| 7 | Head | Skull | Towne | 2 | 2 | 0 | 4 | 1 | 1750 | 0 |
| 8 | Head | Skull | Axial | 2 | 2 | 0 | 4 | 1 | 1750 | 0 |
| 9 | Head | Skull | Waters | 2 | 2 | 0 | 4 | 1 | 1750 | 0 |
| 10 | Head | Skull | | 2 | 2 | 0 | 4 | 1 | 1750 | 0 |
| 11 | Head | Skull | | 1 | 0 | 0 | 4 | 1 | 1750 | 0 |
| 12 | Head | Skull | | 1 | 0 | 0 | 4 | 1 | 1750 | 0 |
| 13 | Head | Sella turcica | A-P | 2 | 2 | 0 | 4 | 1 | 1750 | 0 |
| 14 | Head | Sella turcica | LAT | 2 | 2 | 0 | 4 | 1 | 1750 | 0 |
| ... | | | | | | | | | | |
| 655 | Leg | Sesamoid bones of foot(L) | Frontal | 2 | 1 | 0 | 4 | 1 | 1750 | 0 |
| 656 | Leg | Sesamoid bones of foot(L) | Side | 2 | 1 | 0 | 4 | 1 | 1750 | 0 |
| 657 | Leg | Sesamoid bones of foot(L) | Oblique | 2 | 1 | 0 | 4 | 1 | 1750 | 0 |
| 658 | Leg | Sesamoid bones of foot(L) | Axial | 2 | 1 | 0 | 4 | 1 | 1750 | 0 |
| 659 | Leg | Sesamoid bones of foot(L) | | 1 | 0 | 0 | 4 | 1 | 1750 | 0 |
| 660 | Leg | Sesamoid bones of foot(L) | | 1 | 0 | 0 | 4 | 1 | 1750 | 0 |
| 661 | Leg | Achilles | Right Frontal | 2 | 2 | 0 | 4 | 1 | 1750 | 0 |
| 662 | Leg | Achilles | Right Side | 2 | 2 | 0 | 4 | 1 | 1750 | 0 |
| 663 | Leg | Achilles | Left Frontal | 2 | 2 | 0 | 4 | 1 | 1750 | 0 |
| 664 | Leg | Achilles | Left Side | 2 | 2 | 0 | 4 | 1 | 1750 | 0 |
| 665 | Leg | Achilles | | 1 | 0 | 0 | 4 | 1 | 1750 | 0 |
| 666 | Leg | Achilles | | 1 | 0 | 0 | 4 | 1 | 1750 | 0 |

IMAGE ACQUIRING DISPLAY APPARATUS, METHOD AND APPARATUS FOR EDITING PHOTOGRAPHING CONDITIONS, AND PROGRAM FOR ARRANGING PHOTOGRAPHING CONDITIONS

BACKGROUND OF THE INVENTION

1. Field of the Invention

The invention relates to an apparatus and a method for editing data, and in particular to a system for editing photographing conditions for an image acquiring display apparatus used for diagnosing medical image data, a method for editing photographing conditions by using the image acquiring display apparatus, and a program for arranging photographing conditions.

2. Description of Related Art

A radiographic image acquired by using radiation such as X-ray or the like, has been used widely as a medical image for diagnosing diseases. For example, so-called radiograph which is developed by irradiating X-ray which has transmitted through an object to a phosphor layer (a phosphor screen), and irradiating visible rays generated on the phosphor layer to a film using a silver salt as the same as an usual photograph, has been used as a medical image, in earlier development.

However, recently, a radiographic image converting method has been used, the method for directly extracting the radiographic image as a digital signal by using a radiation detector such as a stimulable phosphor substance, a FPD (Flat Panel Detector) or the like, instead of the film coated with the silver salt. Further, in order to convert the radiographic image acquired by the above-described radiographic image converting method to an image more suitable for the diagnosis, various image processing has been performed to the radiographic image.

More specifically, for example, each of U.S. Pat. No. 3,859,527 and Japanese Patent Application Publication (Unexamined) No. Tokukai-sho 55-12144 discloses a radiographic image converting method which uses a stimulable phosphor substance, and uses visible rays or infrared rays as the stimulative excitation light. The radiographic image converting method uses a radiographic image converting panel wherein a stimulable phosphor layer is formed on a support material. According to the radiographic image converting method, radiation which has transmitted through an object is irradiated to the stimulable phosphor layer, a radiation energy corresponding to a quantity of radiation transmitting through each part of the object is stored in the stimulable phosphor layer, and thereby a latent image is formed on the stimulable phosphor layer. Thereafter, when the stimulable phosphor layer is scanned by the stimulative excitation light such as a predetermined wavelength laser light or the like, the radiation energy stored is emitted as the stimulative light. Therefore, the stimulative light is electrically converted by using a photoelectric conversion element such as a photo-multiplier or the like, and taken out as an electric signal.

The radiographic image diagnostic system which uses the stimulable phosphor substance is commonly called a computed radiographer (CR). The radiographic image diagnostic system can be roughly classified into an erect/supine exclusive type system in which the stimulable phosphor substance is incorporated in a reading apparatus, and a cassette type system using a cassette in which the stimulable phosphor substance is incorporated therein and which can be carried and a reading apparatus for reading the phosphor substance out from the cassette.

In case of photographing the radiographic image by any one of the above-described type radiographic image diagnostic systems, it is necessary to select a suitable photographing condition among a large number of photographing conditions regarding a body part, a photographing direction or the like. The photographing condition is selected by a controller which usually inputs a patient information thereby or displays photographed image data thereon.

The large number of photographing conditions are classified into a plurality of pages, and displayed for every page on a display of the controller. Then, when the page including a desired photographing condition is searched by going to a previous page or a next page in order, with a "previous page" button or a "next page" button, a photographing condition suitable for the photographing of the patient is selected among the photographing conditions included in the searched page and displayed on the display. Further, in case there are an extremely large number of photographing conditions, there is a case the photographing conditions has a hierarchical structure in order to arrange the photographing conditions. In the case, it is possible to find the desired photographing condition by selecting the choices for every hierarchy.

In order to select the photographing condition in the radiographic image diagnostic system, according to the method for going a plurality of pages in order, searing the page including the desired photographing condition and selecting the desired photographing condition among the photographing conditions included in the searched pages, there are problems that the more key operations are required to select the photographing condition included in the following page, and it is impossible to select the desired photographing condition more rapidly, as the photographing conditions increase. Further, the possibility of making an error in selecting the desired photographing condition increases, as the more key operations are required.

Further, according to the method for selecting any one of the choices of the photographing conditions having the hierarchical structure, for every hierarchy, and extracting the desired photographing condition, the number of hierarchies increases, and the number of key operations to find the desired photographing condition increases, as the number of photographing conditions increases. Further, because there is a large difference in the frequency of selecting the photographing conditions in the radiographic image diagnostic system, some photographing conditions are selected extremely frequently, and others are not almost selected. However, in case the photographing conditions have the hierarchical structure, the predetermined number of key operations are required to select the desired photographing condition, regardless of the frequency of selecting the photographing conditions. Therefore, there is a problem it takes the same time to select the photographing condition which is selected frequently, as the time to select the photographing condition which is not almost selected.

Because the above-described radiographic image diagnostic system is used in a medical field such as a hospital or the like, there is a demand for diagnosing just after photographing, and the rapidity is required of the whole system. Further, because there is a case the radiographic image diagnostic system is used in a group medical checkup, the more rapidity is required of the whole system. Furthermore, because the radiation is injurious to the human body, it is necessary to avoid taking a rephotograph caused by an error in photographing, as possible.

Therefore, it is necessary to select the desired photographing condition in a short time. In order to select the photographing condition rapidly, it is thought to reduce the number of photographing conditions to be displayed. However, if the necessary photographing condition is not displayed, the photographing itself may be not taken. On the other hand, because the necessary photographing condition differs with a user, many photographing conditions which are not used by the user are included in the group of photographing conditions generated by extracting and selecting from master data including all photographing conditions. Further, because the photographing conditions to be displayed differ according as the photographing conditions are used continuously, it is necessary to edit the group itself of photographing conditions in order to always display the suitable photographing conditions.

SUMMARY OF THE INVENTION

The present invention was developed in view of the above-described problems.

It is an object of the present invention to provide an image acquiring display apparatus comprising an editing system for photographing conditions, a method of editing photographing conditions by using the apparatus, and a program for arranging photographing conditions, in order to select any of photographing conditions rapidly and certainly.

In order to attain the above-described object, in accordance with a first aspect of the present invention, an image acquiring display apparatus comprises: a display for displaying at least a selection screen for selecting a photographing condition required for a patient from a plurality of photographing conditions, and a display screen for displaying image data read out of a radiographic image conversion medium having a radiographic image of the patient, recorded thereon; and an editing section for editing a plurality of photographing conditions to be displayed on the selection screen, of predetermined master data including a plurality of photographing conditions.

Preferably, in the apparatus of the first aspect of the present invention, a serial number is attached to each of the plurality of photographing conditions included in the master data, the serial number comprising a plurality of classified codes classifiable of each of the plurality of photographing conditions.

More preferably, a combination of at least two selected of at least a body part to be photographed, a modality, a photographing technique, a photographing direction and a print format, is used as the plurality of classified codes.

Preferably, in the apparatus of the first aspect of the present invention or as described above, the editing section generates a first editing screen for extracting a plurality of photographing conditions required for a user, from the plurality of photographing conditions included in the master data, and generating user data peculiar to the user, a second editing screen for modifying or editing a classification of the user data generated, and a third editing screen for modifying or editing each of the plurality-of photographing conditions included in the user data, and changes the first editing screen, the second editing screen and the third editing screen, with switches provided for the first editing screen, the second editing screen and the third editing screen, respectively.

More preferably, an original data display area on which the master data or the user data generated are displayed and a copy data display area on which the user data to be generated are displayed, are contrasted with each other and formed on the first editing screen, each of the original data display area and the copy data display area is provided with an extracting section for extracting the photographing conditions on the basis of each of the classified codes, a searching section for searching the photographing conditions by using the serial number or the photographing conditions, and a rearranging section for rearranging the photographing conditions by using the serial number or the body part of each of the photographing conditions, and the user data are generated by dragging, moving and dropping a predetermined photographing condition from the original data display area to the copy data display area.

Further, preferably, a data display area on which the user data to be generated are displayed, a modality classifying area for specifying the modality of each of the photographing conditions, a body part classifying area for specifying the body part of each of the photographing conditions, and an individual display area on which a photographing condition to which the serial number comprising classified codes of the modality specified and the body part specified is attached, is displayed, are formed on the second editing screen, the data display area is provided with an extracting section for extracting the photographing conditions on the basis of each of the classified codes, and a searching section for searching the photographing conditions by using the serial number or the photographing conditions, and the classification of the user data is modified by dragging, moving and dropping a predetermined photographing condition from the data display area to the individual display area.

More preferably, a plurality of photographing conditions selected on the data display area are moved to the individual display area, together, and registered in the user data, as a set of conditions.

Further, preferably, an input condition area on which a type of an apparatus for reading the image data, a reading condition and a read image are displayed, and an output condition area on which a type of an apparatus for outputting the image data, an output condition, an image processing condition and an output image are displayed, are formed on the third editing screen, and a photographing condition selected, is edited on the input condition area or the output condition area.

Preferably, the apparatus of the first aspect of the present invention, further comprises: an extracting section for extracting a predetermined classified code from the plurality of classified codes of the serial number, with reference to the serial number; a code determining section for determining a value of the predetermined classified code of each of the plurality of photographing conditions to be displayed on the selection screen, according to a frequency or a date of selecting each of the plurality of photographing conditions; an order determining section for determining an order of displaying the plurality of photographing conditions, with reference to the value of the predetermined classified code of each of the plurality of photographing conditions; and a position determining section for determining a position of displaying each of the plurality of photographing conditions on the selection screen, on the basis of the order.

In accordance with a second aspect of the present invention, an apparatus for editing photographing conditions, comprises: an editing section for editing a plurality of photographing conditions required for a user, of predetermined master data including a plurality of photographing conditions required for a patient.

In accordance with a third aspect of the present invention, a method for editing photographing conditions, comprises: displaying an editing screen for editing a plurality of photographing conditions required for a user, of predetermined master data including a plurality of photographing conditions required for a patient; and editing the plurality of photographing conditions required for the user, of the predetermined master data, on the editing screen.

In accordance with a fourth aspect of the present invention, a method for editing photographing conditions, for an image acquiring display apparatus which displays at least a selection screen for selecting a photographing condition required for a patient from a plurality of photographing conditions, and a display screen for displaying image data read out of a radiographic image conversion medium having a radiographic image of the patient, recorded thereon, comprises: displaying an editing screen for editing a plurality of photographing conditions to be displayed on the selection screen, of predetermined master data including a plurality of photographing conditions; and editing a plurality of photographing conditions required for a user, of the predetermined master data, on the editing screen.

In accordance with a fifth aspect of the present invention, a program for arranging photographing conditions, makes an image acquiring display apparatus perform processing, the image acquiring display apparatus comprising: a display for displaying at least a selection screen for selecting a photographing condition required for a patient from a plurality of photographing conditions, and a display screen for displaying image data read out of a radiographic image conversion medium having a radiographic image of the patient, recorded thereon; and an editing section for editing a plurality of photographing conditions to be displayed on the selection screen, of predetermined master data including a plurality of photographing conditions, the processing comprising: extracting a predetermined classified code from a plurality of classified codes of a serial number attached to each of the plurality of photographing conditions included in the master data, with reference to the serial number; determining a value of the predetermined classified code of each of the plurality of photographing conditions to be displayed on the selection screen, according to a frequency or a date of selecting each of the plurality of photographing conditions; determining an order of displaying the plurality of photographing conditions, with reference to the value of the predetermined classified code of each of the plurality of photographing conditions; and determining a position of displaying each of the plurality of photographing conditions on the selection screen, on the basis of the order.

According to the above-described present invention, because the serial number comprising a plurality of classified codes determined in consideration of the characteristic of the radiation diagnosis, is attached to the photographing condition, it is possible to classify the photographing conditions variously. Further, because the first editing screen for generating the group of photographing conditions peculiar to the user, from the photographing conditions included in the master data including all the photographing conditions, the second editing screen for reviewing or modifying the classification of the group of photographing conditions peculiar to the user, or the third editing screen for reviewing or modifying each of the photographing conditions, is used as the editing screen, and the photographing conditions are edited by being dragged and dropped on the editing screen, it is possible that the user edits the group of photographing conditions easily, by himself.

Furthermore, because the value of the predetermined classified code is determined according to the frequency of selecting the photographing condition, and the order of displaying the photographing conditions is rearranged with reference to the determined value of the predetermined classified code when generating the editing screen, according to the program for arranging photographing conditions, it is possible that the user always selects the photographing conditions on the screen suitable for the used state.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein:

FIG. 4 is a view showing a waiting list screen 14 for the patient information, displayed on the controller 8;

FIGS. 5A, 5B, 5C and 5D are views showing selection screens 15 for photographing conditions, displayed on the controller 8;

FIG. 9 is a view showing a photographing condition editing screen (master editing screen 19) displayed on the controller 8;

FIG. 10 is a view showing a photographing condition editing screen (condition key editing screen 20) displayed on the controller 8;

FIG. 11 is a view showing a photographing condition editing screen (condition editing screen 21) displayed on the controller 8;

FIG. 15 is a table showing exemplary consecutive numbers attached to the photographing conditions.

PREFERRED EMBODIMENTS OF THE INVENTION

Hereinafter, a preferred embodiment of the present invention will be explained with reference to figures.

An image acquiring display apparatus of the present invention, according to a preferred embodiment, has a screen for specifying an information of a patient as an object of a radiographic image diagnosis, a screen for selecting photographing conditions to be used for photographing the patient from a plurality of photographing conditions, and a screen for displaying image data read out of a radiographic image conversion medium having a radiographic image of the patient, recorded thereon. The serial number comprising a plurality of classified codes such as a body part to be photographed, a modality, a photographing technique, a photographing direction, a print format or the like, which is determined in consideration of a characteristic of the radiation diagnosis, is attached to each of the photographing conditions. Accordingly, it is possible to classify the photographing conditions variously, by using the classified codes. Further, a master editing screen on which the user arbitrarily extracts photographing conditions from master data including a plurality of photographing conditions, determined by a maker, and generates user data, a condition key editing screen for modifying or editing a classification of the user data generated, and a condition editing screen for modifying or editing each of the photographing conditions included in the user data, are provided as an editing screen for the photographing conditions. Accordingly, because the photographing conditions are copied by being dragged and dropped, or a set of photographing conditions is determined, on the editing screen, it is possible that the user generates the user data easily, by himself. Further, because the editing screen for the photographing conditions is optimized and displayed, it is possible that the user selects the photographing conditions smoothly.

Embodiment

In order to explain the above-described embodiment of the present invention in more detail, the preferred embodiment of the present invention will be explained with reference to FIGS. 1 to 8.

Figure 1:
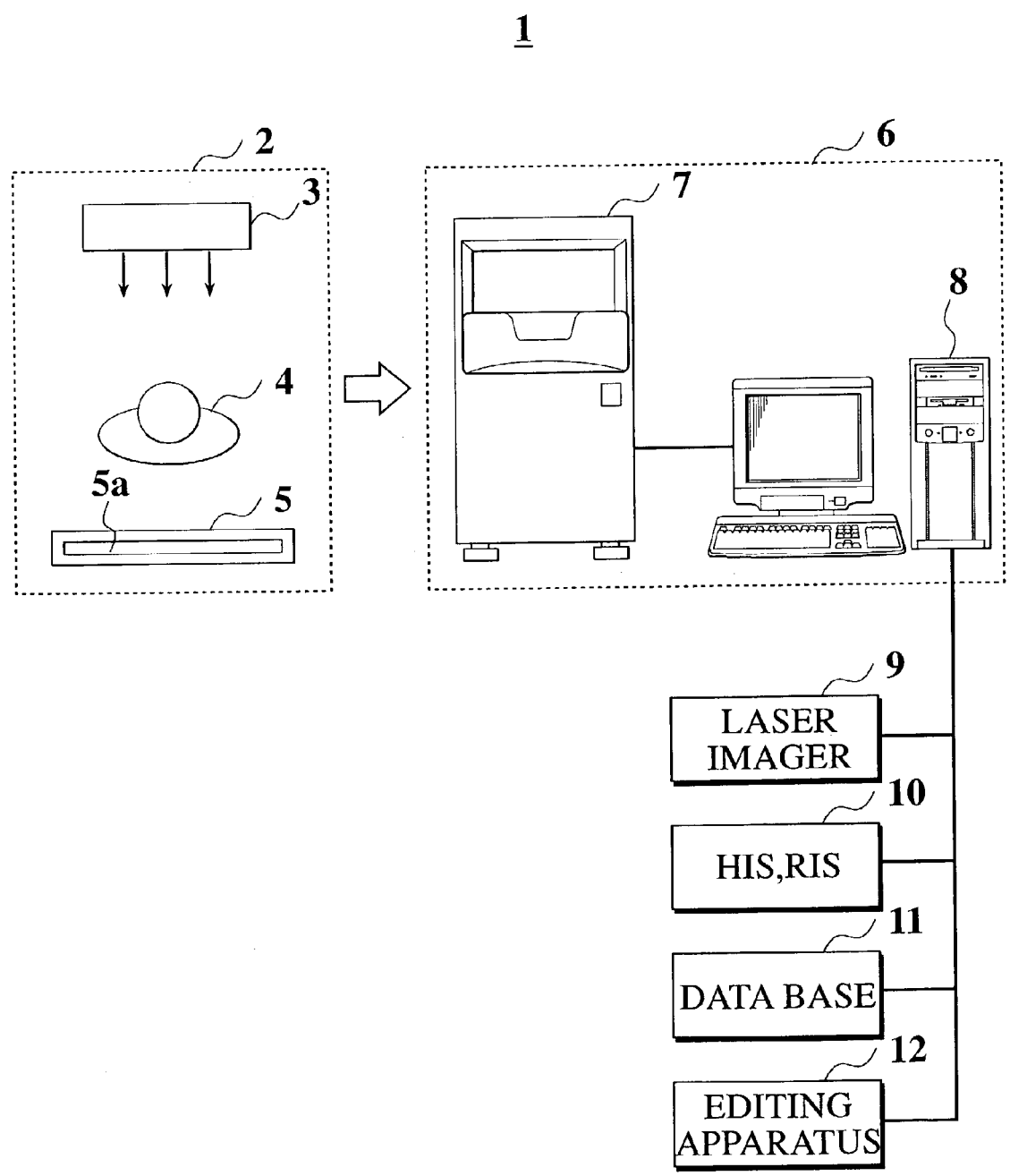
FIG. 1 is a diagram showing a whole structure of a radiographic image diagnostic system 1 according to the present invention.
Figure 2:
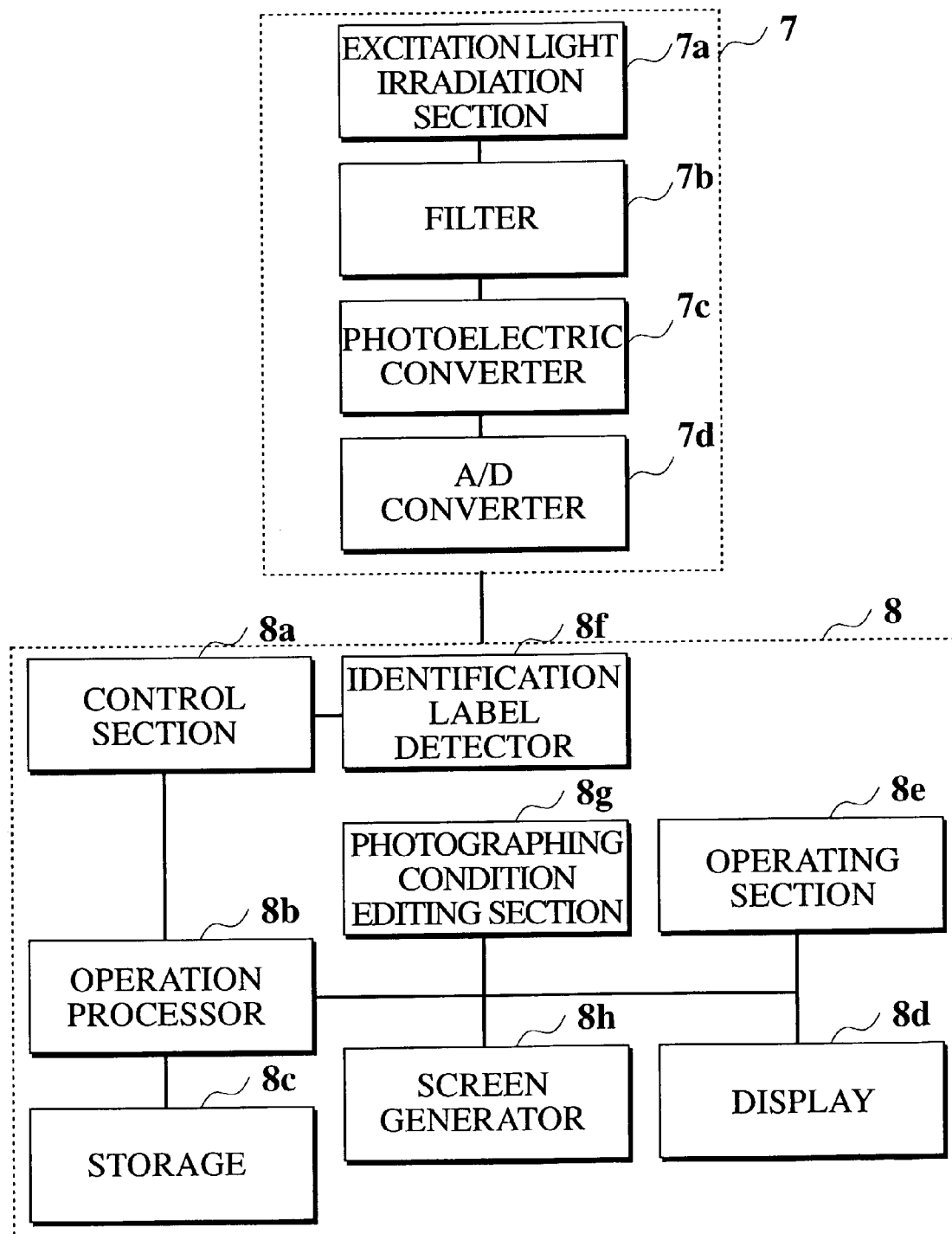
FIG. 2 is a block diagram showing a structure of an image acquiring display apparatus 6 composing the radiographic image diagnostic system 1.

FIG. 1 is a diagram showing a whole structure of a radiographic image diagnostic system 1. FIG. 2 is a block diagram showing a structure of an image acquiring display apparatus 6 composing the radiographic image diagnostic system 1. FIGS. 3 to 8 are views showing exemplary structures of screens which are displayed on a controller 8 of the image acquiring display apparatus 6.

In the following explanation, it will be described that an editing system of photographing conditions, which is characteristic of the present invention is provided for a controller of a cassette type of image acquiring display apparatus. However, the above-described editing system can be provided for a controller of any apparatus for displaying a medical image, such as a system which uses a radiographic image conversion medium other than a cassette, an erect/supine exclusive type system which uses fixed radiographic image conversion medium, a system which directly extracts a radiographic image as a digital image by using such a radiation detector as a FPD, or the like. Further, the editing system can be provided for an editing apparatus which is connected to the apparatus for displaying a medical image through a network, and operates.

First, in order to make the editing system of photographing conditions, which is characteristic of the present invention, understood more easily, the structure of the radiographic image diagnostic system, the structure of the image acquiring display apparatus, and a photographing method by using a radiographic image diagnostic system, will be introduced.

As shown in FIGS. 1 and 2, the radiographic image diagnostic system 1 comprises a X-ray photographing apparatus 2 which photographs the object with X-ray, and an image acquiring display apparatus 6 which reads and displays the X-ray image photographed by the X-ray photographing apparatus 2.

In the X-ray photographing apparatus 2, when a X-ray irradiation apparatus 3 comprising a X-ray tube or the like, irradiates X-ray, the irradiated X-ray transmits through an object 4, and is irradiated to a radiographic image conversion medium such as a radiographic image conversion panel 5a or the like, which is incorporated in a cassette 5. The radiographic image conversion panel 5a has a stimulable phosphor layer. When the X-ray is irradiated to the stimulable phosphor layer, a part of an energy of the X-ray is stored in the stimulable phosphor layer, as a latent image, according to a quantity of the irradiated X-ray.

After the X-ray photograph, when the cassette 5 incorporating the radiographic image conversion panel 5a in which the latent image is formed, is thrown in an image reading apparatus (a reader 7) of the image acquiring display apparatus 6, the reader 7 takes the radiographic image conversion panel 5a out of the cassette 5. Then, when an excitation light irradiation section 7a of the reader 7 irradiates the excitation light such as visible rays, infrared rays or the like, to the radiographic image conversion panel 5a, the radiographic image conversion panel 5a emits the stimulative light according to the energy quantity of the X-ray which is stored in the stimulable phosphor substance. When the emitted stimulative light is inputted to a photoelectric converter 7c through a filter 7b, the photoelectric converter 7c converts the stimulative light to a voltage signal in proportion to the intensity of the stimulative light, and outputs the voltage signal to an A/D converter 7d. Then, the A/D converter 7d converts the voltage signal to digital image signal data, and outputs the digital image signal data to a controller 8.

The controller 8 comprises a display 8d such as a CRT or the like, and an operating section 8e such as a key board, a touch panel or the like. The controller 8 makes a storage 8c store the digital image signal data outputted from the A/D converter 7d, outputs it to the display 8d such as the CRT or the like, and sends and outputs it as a film to a laser imager 9 which is connected thereto through the DICOM network.

Further, the controller 8 comprises a control section 8a for controlling the reader 7 on the basis of the reading condition determined, an operation processor 8b for performing various image processing (a correcting processing, a gradation converting processing, a trimming, a reverse/rotation, a parameter change, a masking or the like) to the image read by the reader 7, a screen generator 8h for generating various screens such as a waiting list screen, a search screen, a photographed body part selection screen, a photographing routine screen or the like, an identification label detector 8f for reading a plate ID of the cassette 5, and a photographing condition editing section 8g for editing the photographing conditions which is characteristic of the present invention.

Herein, although the reader 7 and the controller 8 are shown in a state they are separated from each other, in figures, they may be as one, and compose the image acquiring display apparatus 6. Further, the controller 8 can be connected to the terminal 10 of the HIS (hospital information system), the RIS (radioactive information system) or the like, for inputting or outputting remote patient information through the network, or a data base 11 for storing photographing history information or the like. Furthermore, the controller 8 can be provided with an editing apparatus 12 which is separated from the editing system of the present invention.

The above-described cassette type radiographic image diagnostic system 1 adopts any one of a method (pre-registration) for photographing after previously registering the relationship between the cassette 5 and reservation information which are the patient information, the photographing conditions, the reading conditions or the like, in order to define the relation ship, and a method (post-registration) for relating the order of inputting the cassette and the order of inputting the reservation information without registering the cassette 5 before photographing by radiation. Therefore, the radiographic image diagnostic system 1 reads the image data.

The pre-registration and the post-registration have characteristic effects, respectively. For example, in a hospital or the like, wherein a large number of readers 7 and controllers 8 are provided for various positions, and a large number of radiologists photograph, it is possible to diagnose radiographic images of a large number of patients, accurately, according to the pre-registration. On the other hand, in a hospital of a general practitioner or the like, wherein a small number of readers 7 and controllers 8 are provided, and a small number of radiologists photograph, it is possible to photograph the object by the X-ray, rapidly and efficiently, according to the post-registration.

Herein, the editing system of photographing conditions, which is characteristic of the present embodiment, can be applied to an apparatus which adopts any one of the registration methods.

Hereinafter, the method of photographing the patient by using the radiographic image diagnostic system 1 having the above-described structure, and diagnosing the patient by using the acquired image will be explained with reference to exemplary screen structures shown in FIGS. 3 to 8. Further, the importance of the operation of selecting the photographing conditions and the necessity of editing the photographing conditions will be explained as follows.

Figure 3:
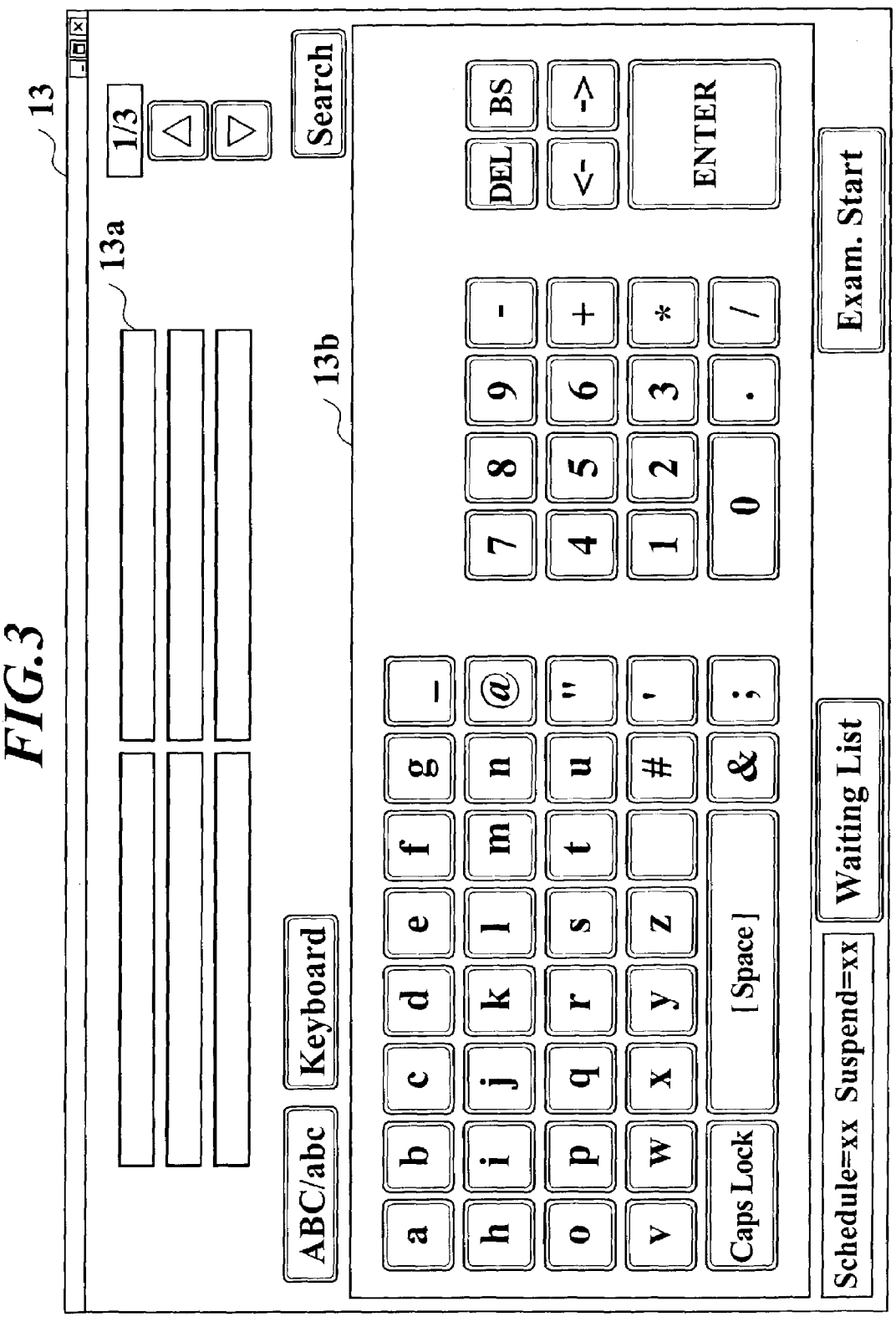
FIG. 3 is a view showing a search screen 13 for patient information, displayed on a controller 8 of the image acquiring display apparatus 6.

First, an operator such as a radiologist or the like inputs patient information with the display 8*d* and the operating section 8*e* of the controller 8. Herein, a search screen 13 shown in FIG. 3 is set as an initial screen. When the operator enters a predetermined search key with a keyboard displayed on an input area 13*b*, and touches or clicks a "Search" button, the patient information is searched with reference to an external information terminal such as the HIS, the RIS or the like, the data base or the like, and displayed on a display area 13*a*.

Further, the patient information can be acquired with a waiting list screen 14. In this case, when the operator touches a "Waiting List" button on the search screen 13 shown in FIG. 3, the waiting list screen 14 shown in FIG. 4 is displayed. As shown in FIG. 4, the patient information such as a patient ID, a patient name, a sex, an age, a department, a location, a photographing condition, sheets (total) of images to be photographed, or the like are displayed as a list, on a display area 14*a* of the waiting list screen 14. Then, the operator selects a patient information of a predetermined patient to be photographed, from the patient information of the list displayed. Then, the waiting list screen 14 is changed to the search screen 13 with a "OK" button. When the operator selects a "Exam. Start" button provided for the search screen 13, to start the examination, a photographing condition selection screen 15 is displayed.

The photographing condition is a condition which should be considered when photographing a patient by radiation rays. It is possible to acquiring a suitable radiographic image by photographing a patient on the basis of the selected photographing conditions. For example, the photographing condition is the body part of the human body to be photographed (the head, the chest, the abdomen, the neck, the hips, the spine, the lungs, the arm, the leg, or the like), a posture when photographing the body part of the human body (the erect, the supine or the like), a photographing direction (the frontal, the side or the like), a characteristic of a patient (the sex, the age, the physique or the like), a name of a disease, or the like.

Further, the large number of photographing conditions are provided as data (maker master data) including all conditions, by a maker providing the system. Therefore, in order to display all several hundred photographing conditions on the screen, the screens are required down to several pages. Accordingly, it is difficult to rapidly select the suitable photographing conditions for the patient from the photographing conditions displayed on a large number of pages. As a result, the maker usually extracts only the photographing conditions which are used by a user, from all the photographing conditions, generates the screen wherein the extracted photographing conditions are classified so that the operator can select easily, and provides the screen to the user.

Figure 5A:
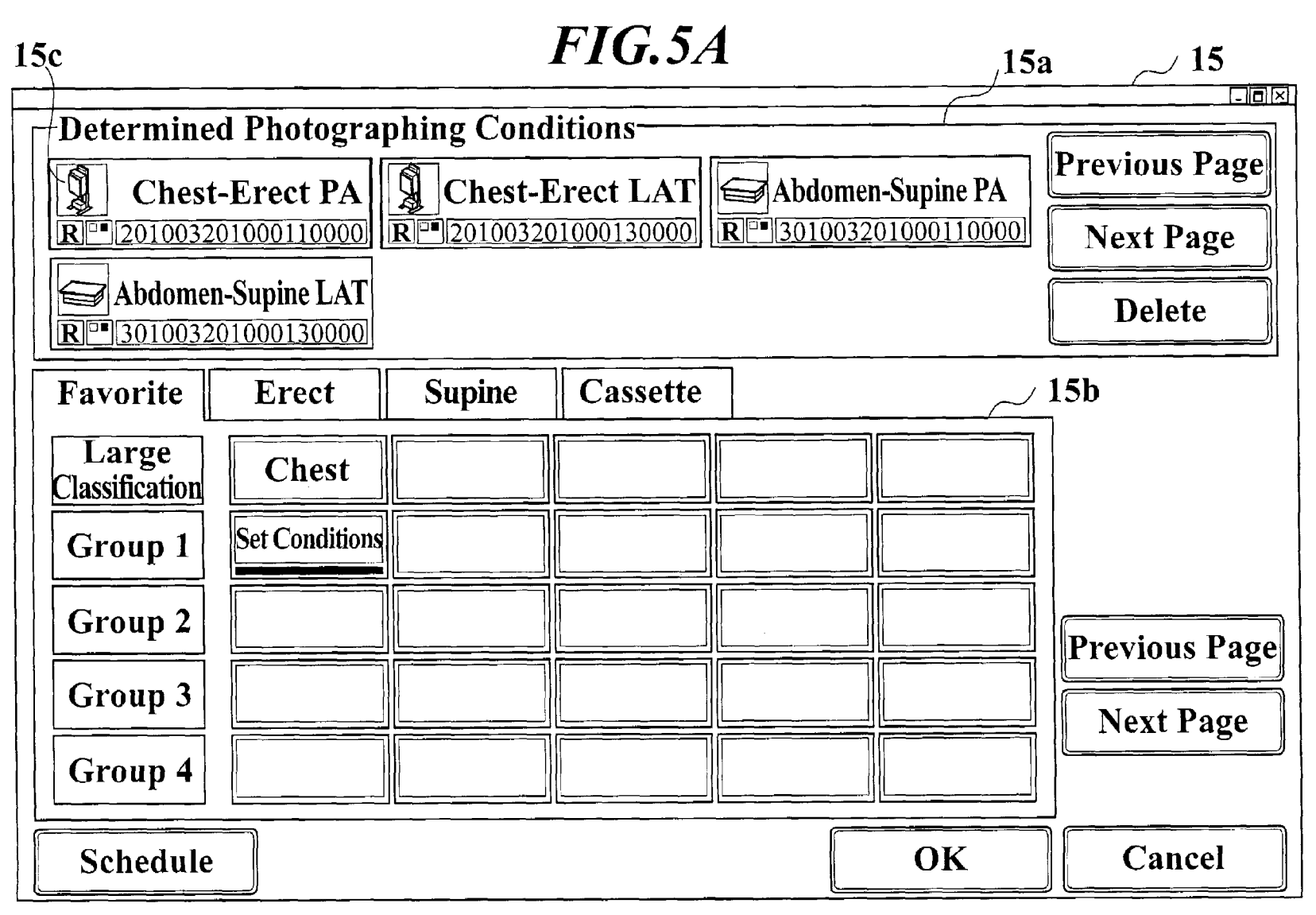

As the screen wherein the photographing conditions are classified, the photographing condition selection screen 15 as shown in FIG. 5A is displayed. For example, a determined condition display area 15*a* on which the photographing conditions which are used specially frequently among the extracted photographing conditions, are displayed, and a classified condition display area 15*b* on which the photographing conditions which are classified for every photographing state such as the posture when photographing the body part, the body part to be photographed or the like, are displayed, are provided for the photographing condition selection screen 15. For example, the erect photographing condition which is used frequently, is displayed with an erect icon 15*c*, on the determined condition display area 15*a*. Therefore, when the operator selects any photographing conditions from the photographing conditions displayed on the determined condition display area 15*a*, or selects any classification from the erect, the supine, the cassette and so on displayed on the classified condition display area 15*b*, the operator touches a "Previous Page" button, a "Next Page" button or the like. Thereby, when the screen including the desired photographing conditions is displayed, the operator selects the desired photographing conditions from those displayed on the screen, as the occasion may demand.

Figure 5B:
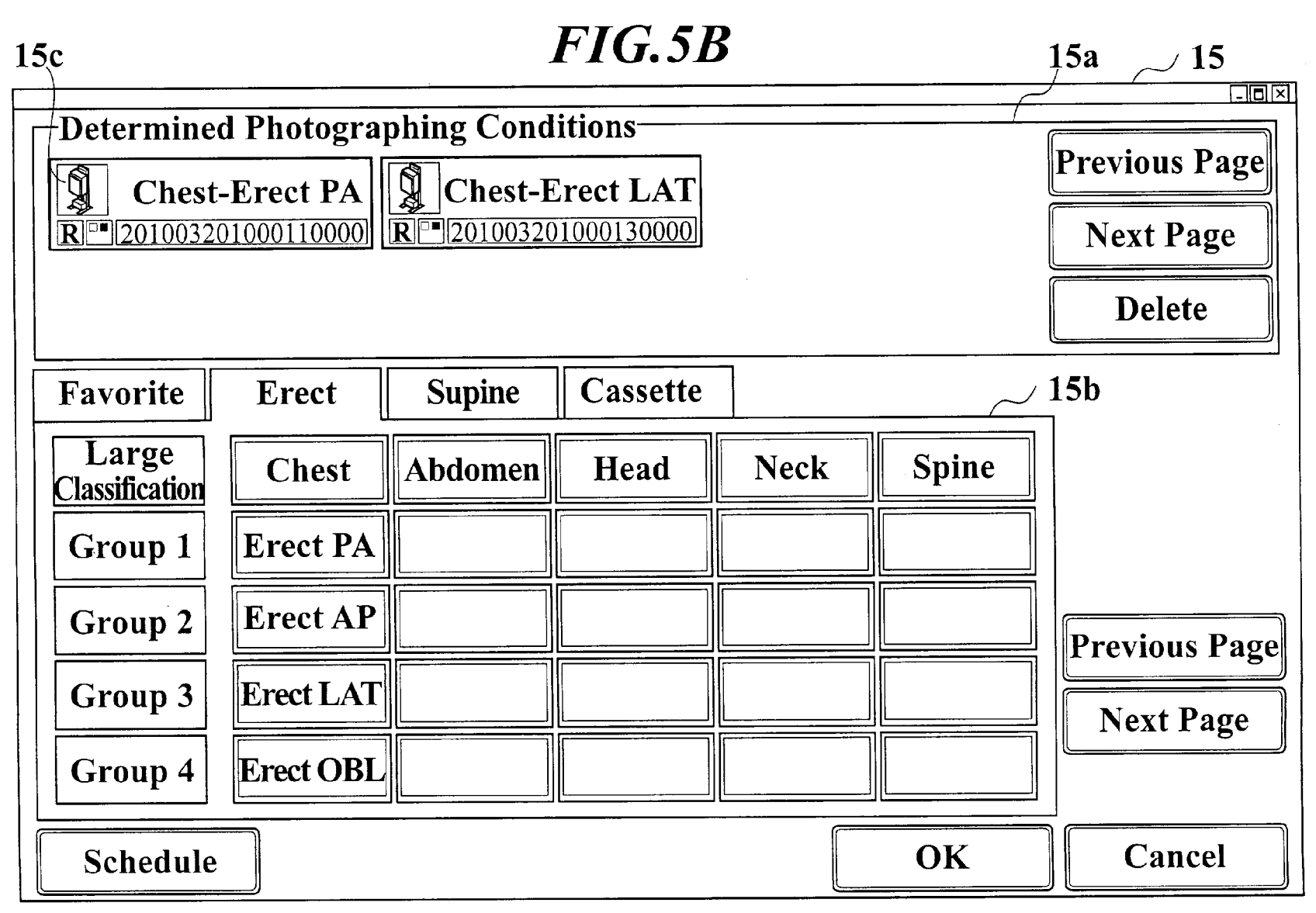

For example, when the operator selects the erect on the classified condition display area 15*b* of the photographing condition selection screen 15, the screen is displayed as shown in FIG. 5B, so as to include the photographing conditions classified into the erect, as suitable photographing conditions for the photograph at the erect state. Further, the photographing conditions displayed on the screen may be classified for every body part to be photographed so that the operator selects the desired photographing condition easily in consideration of the erect photographing posture, and displayed on the screen. For example, regarding the erect, because there are many cases of photographing the chest, the abdomen, the head and so on, the photographing conditions may be displayed so that the operator can select the photographing conditions classified into those easily. As well, when the operator selects the supine or the cassette on the classified condition display area 15*b*, the screen is displayed as shown in FIG. 5C or 5D, so as to include the photographing conditions classified into the supine or the cassette, as suitable photographing conditions for the photograph at the supine state or with the cassette. In the case, the photographing conditions displayed on each screen may be classified for every body part to be photographed so that the operator selects the desired photographing condition easily in consideration of the supine or the cassette, and displayed on the screen. For example, regarding the supine or cassette, in order to photograph the patient who cannot be photographed at the erect state (for example, the patient who cannot stand or the like), the photographing conditions may be classified in order from the head, following the structure of the human body, so that any body part of the patient can be easily photographed as it is, and displayed on the screen.

Because the above-described photographing condition selection screen 15 is generated in consideration of the operation of the operator, it is easy to select the desired photographing condition on the arranged screen. However, the kind or number of photographing conditions desired to be extracted from the maker master data differs according to the user, there occurs a difference in the frequencies of selecting the photographing conditions as the photographing conditions have been used continuously, or new photographing condition is used. Accordingly, there is a case the user requires to review the photographing conditions, or to modify the screen structure.

In the case, conventionally, because only the maker side can perform an operation for extracting the desired photographing conditions from the maker master data, an operation for correcting the order of displaying the photographing conditions, or the like, the user side cannot perform the operation. However, if the user by himself can perform the above-described operation, it is possible to reduce the time required to obtain the desired data after the user requests the above-operation of the maker. Further, it is possible that the user generates the screen according to the necessary, by himself, so as to use it easily as the occasion may demand, and immediately selects the desired photographing conditions on the screen and photographs the patient according to the photographing conditions. However, as described above, because the maker master data includes several hundred photographing conditions, it is difficult that the user extracts the necessary photographing conditions from those. Further, there has not been any image acquiring display apparatus and any editing apparatus comprising the editing system supporting the editing operation.

The background that it is difficult to edit the photographing conditions is that serial numbers which are attached to the photographing conditions respectively are consecutive numbers which are provided for the photographing conditions in order, or that the photographing conditions cannot be searched or rearranged efficiently because the structure of the classifiable codes which are provided for the photographing conditions coincides with the characteristic of the radiation diagnosis. For example, as shown in FIG. 15, the consecutive members are attached to the photographing conditions of the head as a top body part to be photographed to the leg as a bottom body part, in order.

Therefore, according to the embodiment, it is possible to classify the photographing conditions variously by attaching the serial number which is composed of a plurality of classified codes determined in consideration of the characteristic of the radiation diagnosis, to each photographing condition. Further, it is possible to solve the above-described problems by providing the edition screen wherein a user inexperienced in a mechanical operation can easily search or extract the desired photographing condition. The specific structure will be explained according to the following embodiment.

The photographing method will be explained. When the operator selects the desired photographing conditions, and after touches the "OK" button on the photographing condition selection screen 15, the identification label information (plate ID) which the identification label detector 8f of the controller 8 has read out of the cassette 5 is related to the photographing conditions and the reading conditions. Then, when the radiographic image photographing apparatus such as the X-ray photographing apparatus 2 or the like, photographs the selected patient, the X-ray transmitted image of the patient is stored in the radiographic image conversion panel 5a of the cassette 5, as the latent image.

Next, when the operator such as a radiologist or the like takes the cassette 5 out of the X-ray photographing apparatus 2, and inserts the taken cassette 5 into an arbitrary slot of the reader 7, the reader 7 reads the plate ID, searches the data base on the basis of the plate ID as the search key, and extracts the reading condition corresponding to the plate ID, in case of the pre-registration. On the other hand, the reader 7 extracts the reading condition corresponding to the cassette 5 on the basis of the relationship between the cassette insertion queue and the reservation selection queue in case of the post-registration. Thereafter, the reader 7 reads the latent image of the radiographic image conversion panel 5a, according to the determined reading condition.

According to the method of reading the image data, first, the carrier speed of the plate carrier system or the sampling pitch of the A/D converter 7d is determined, according to the reading sensitivity or the reading resolution determined as the reading condition. Then, when the radiographic image conversion panel 5a is taken out of the cassette 5, the scanning system reads the image data stored and kept in the radiographic image conversion panel 5a, by scanning the radiographic image conversion panel 5a.

Then, when the excitation light is operated on the radiographic image conversion panel 5a, the energy stored in the phosphor substance is emitted as the stimulative light. Thereafter, when the photoelectric converter 7c gathers and converts the stimulative light to the electric signal, the logarithmic converter converts the electric signal to the logarithmic signal (thereby, the electric signal which is linear to the optical sensitivity of the stimulative light is converted to the electrical signal which is logarithmically linear to the optical sensitivity of the stimulative light, that is the electric signal which is linear to the density.). Further, the A/D converter 7d converts the logarithmic signal to the digital signal.

The operation processor 8b processes the correcting processing (the shading correcting, the unevenness correcting caused by the stimulative light generator, the sensitive unevenness correcting of the radiographic image conversion panel, or the like), the gradation converting processing or the like, which is specific to the image acquiring display apparatus 6 or the radiographic image conversion panel 5a, to the image data outputted from the A/D converter 7d.

Figure 6:
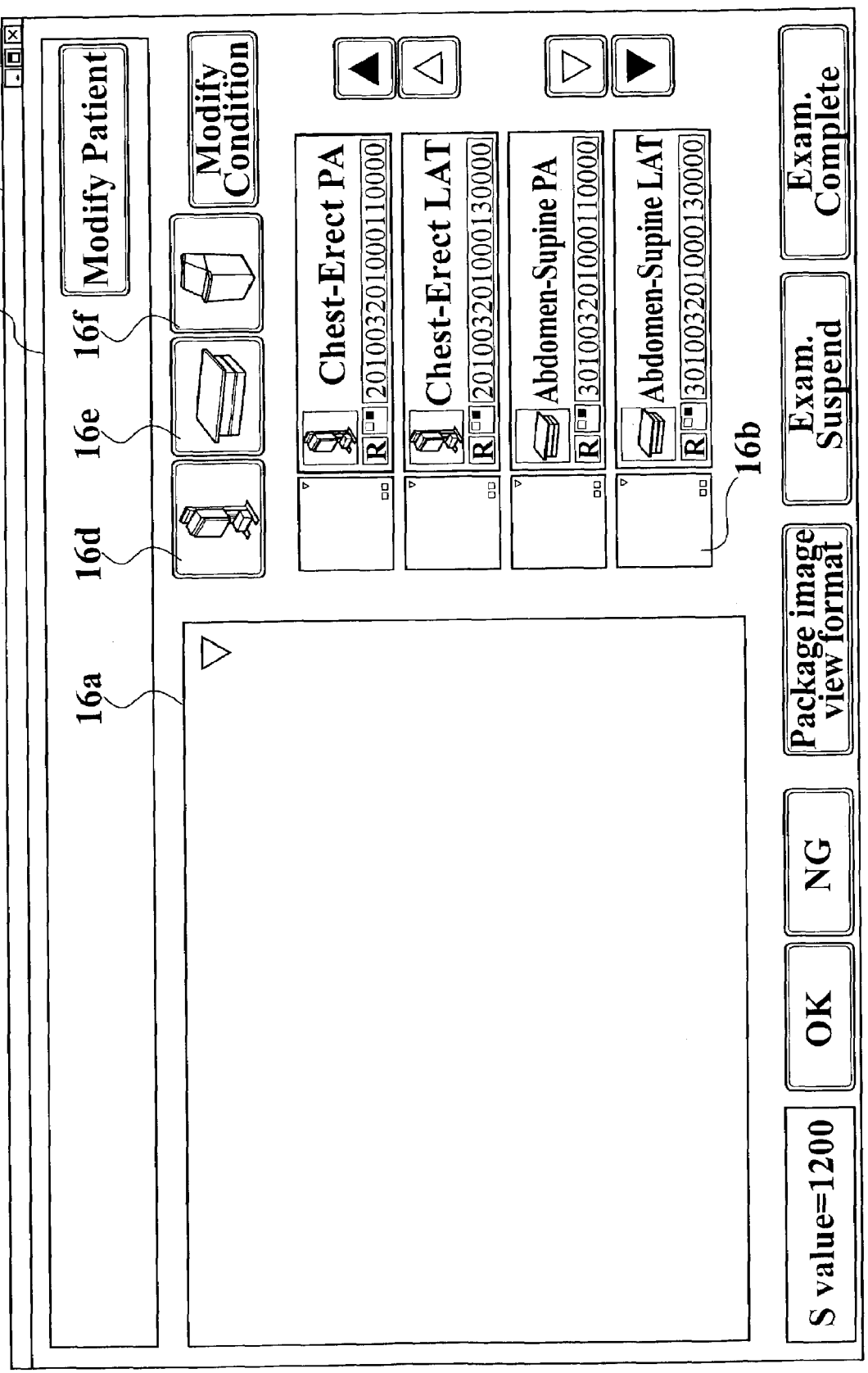
FIG. 6 is a view showing one image view format of image data display screen 16 displayed on the controller 8.
Figure 7:
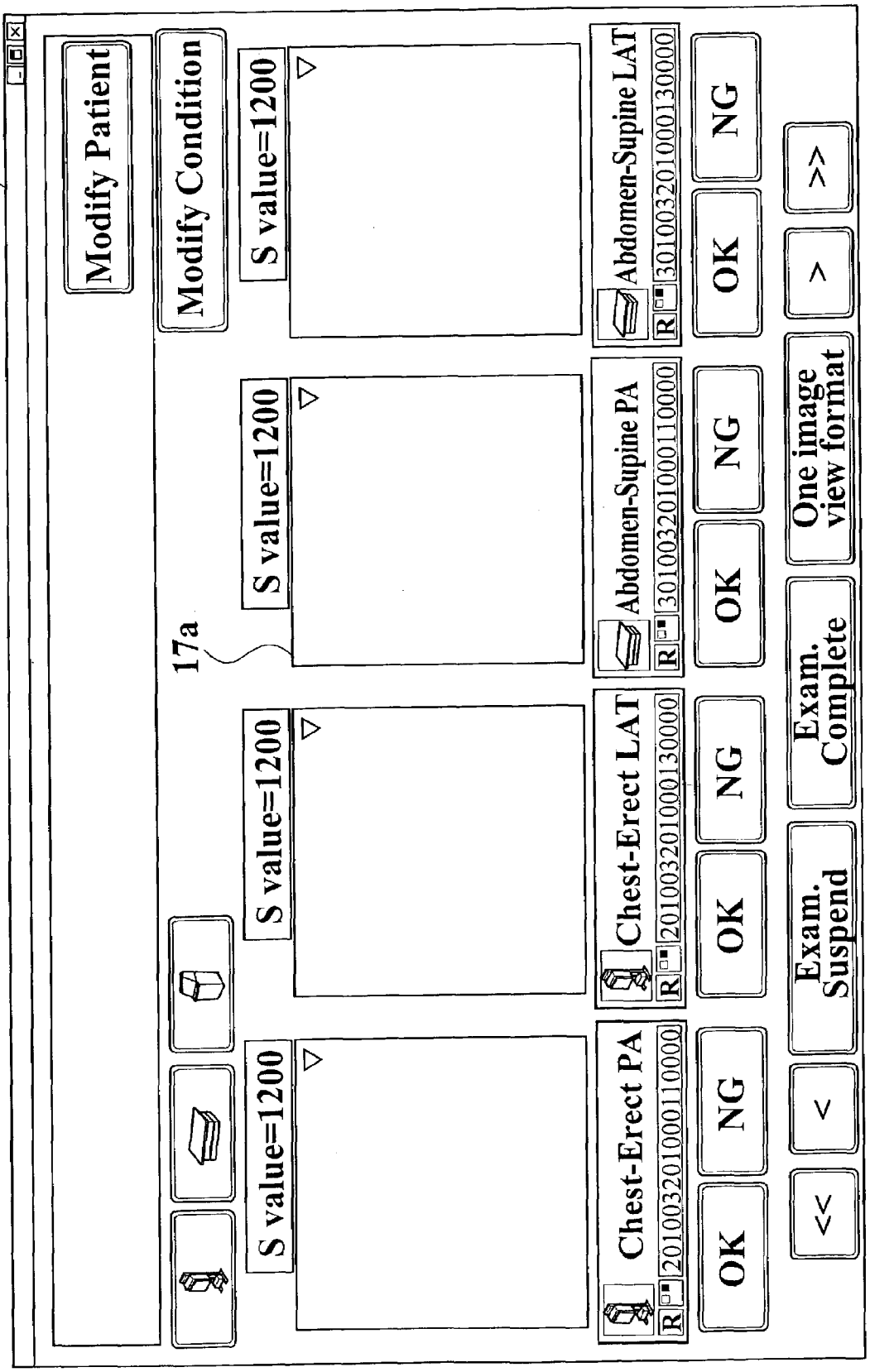
FIG. 7 is a view showing a package image view format of image data display screen 17 displayed on the controller 8.
Figure 8:
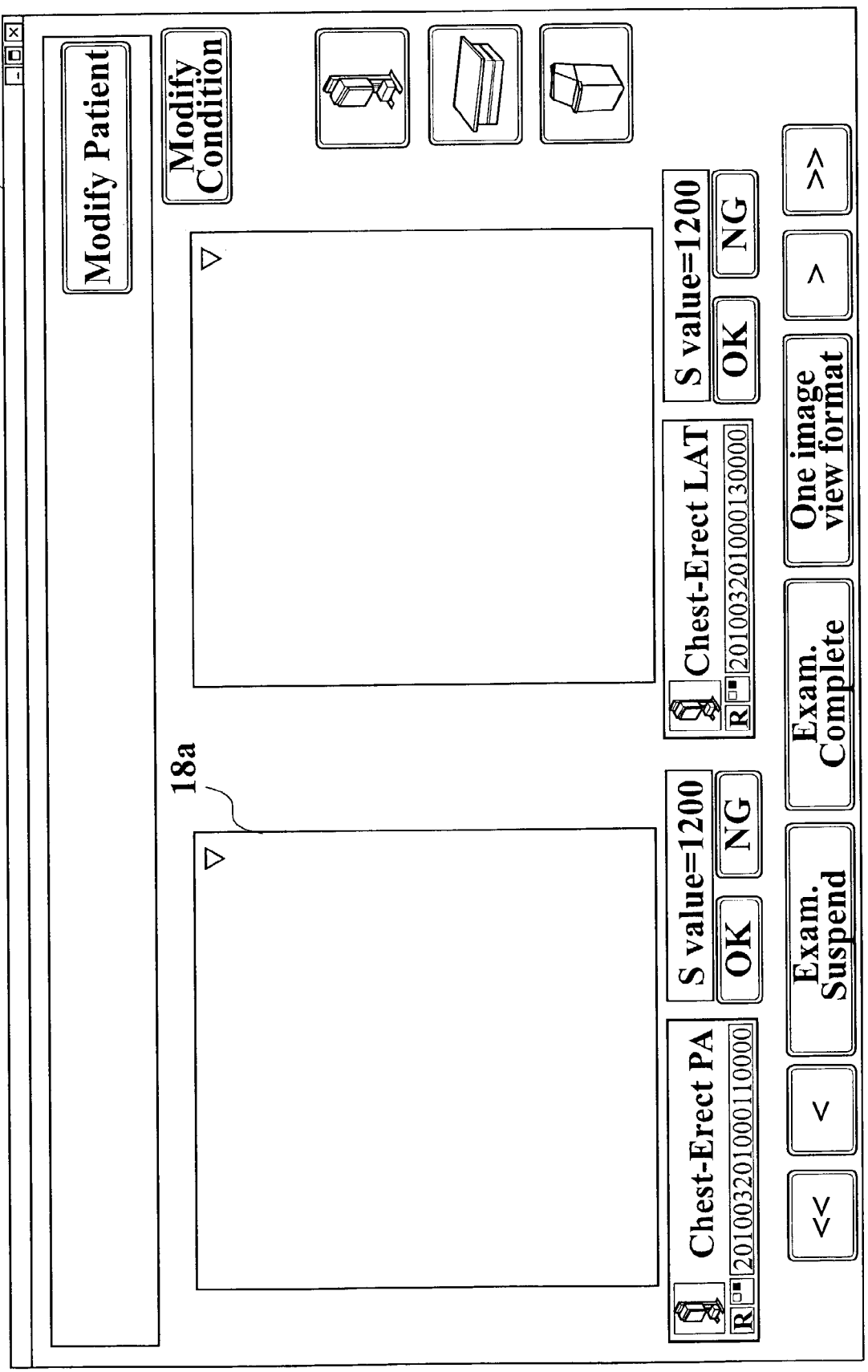
FIG. 8 is a view showing a package image view format of image data display screen 18 displayed on the controller 8.

Thereafter, the photographing routine screens shown in FIGS. 6 to 8 are displayed.

FIG. 6 shows one image view format of photographing routine screen 16 comprising a main display area 16a on which representative image data are displayed, sub display areas 16b on which image data photographed in connection with the representative image data are reduced in the thumbnail format and displayed, a patient information display area 16c on which the inputted patient information is displayed. FIG. 7 is a package image view format of photographing routine screen 17 comprising image display areas 17a on which a plurality of same size of images (four images in case shown in FIG. 7) are displayed. FIG. 8 is a package image view format of photographing routine screen 18 comprising image display areas 18a on which two same size of images are displayed. Further, various buttons may be provided so as to modify the photographing conditions for every classification such as the erect, the supine, the cassette or the like, for each photographing routine screen. For example, an erect icon 16d, a supine icon 16e, a cassette icon 16f and so on, are provided for the photographing routine screen 16.

Therefore, when any display format suitable for the diagnosis is selected from the above-described display formats as the occasion may demand, the photographed image data are displayed in the selected display format, and the patient's case is diagnosed on the basis of the displayed image data.

A series of operations as described above are done continuously, and thereby the patient's case is diagnosed. However, in order to photograph the medical image urgently, or prevent from missing selecting the photographing conditions, it is required to display the necessary and sufficient photographing conditions according to the state used by the user on the photographing condition selection screen.

Hereinafter, the photographing condition editing system will be explained that a user himself extracts desired photographing conditions from the maker master data, and acquires the desired photographing condition selection screen.

First Embodiment

First, the image acquiring display apparatus comprising the editing system of the photographing conditions according to the first embodiment of the present invention, and the method for editing the photographing conditions by using the image acquiring display apparatus, will be explained with reference to FIGS. 9 to 12.

Figure 12:
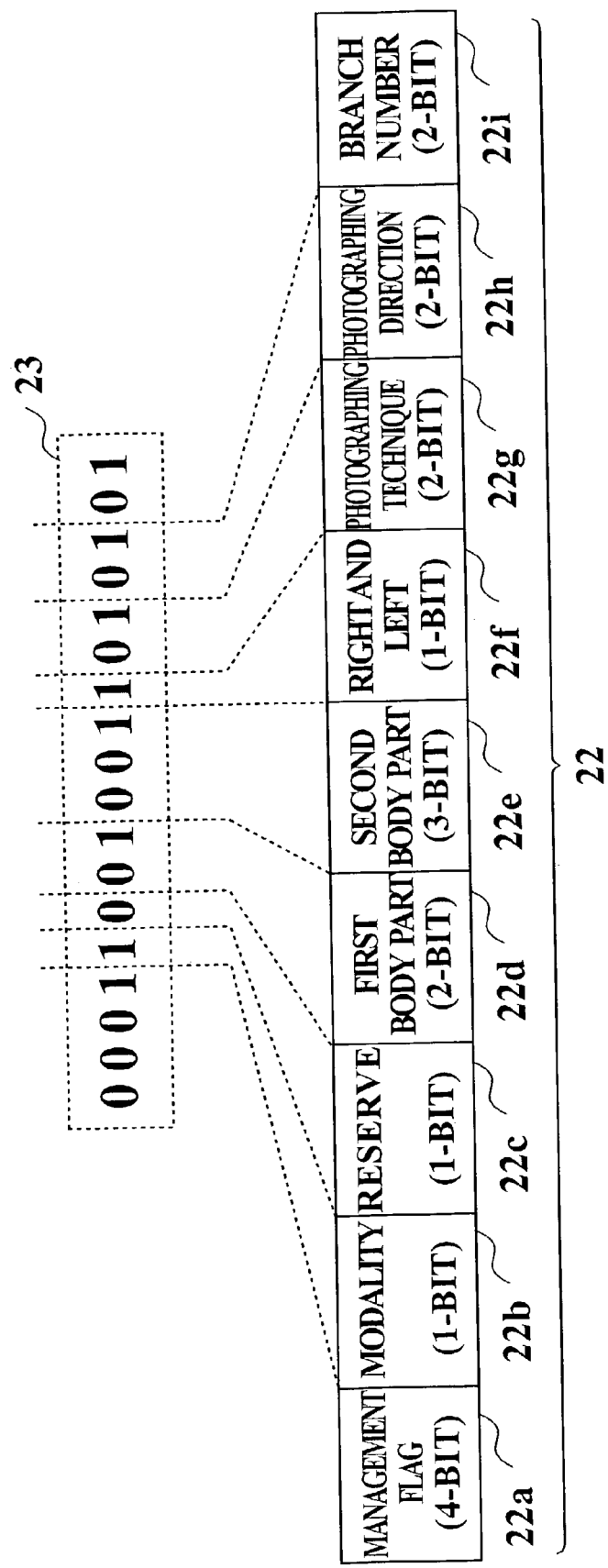
FIG. 12 is a view showing a structure of classified codes 22 attached to each of photographing conditions according to a first embodiment of the present invention.

FIGS. 9 to 11 are views showing exemplary structures of screens displayed on the controller 8 when editing the photographing conditions according to the first embodiment. FIG. 12 is a view showing a structure of classified codes which are attached to the photographing conditions.

As described above, there are various types photographing conditions. In order to satisfy the demand of each user, the maker master data which are predetermined by the maker is required to include all the photographing conditions. As a result, because the photographing conditions are divided into a large number of pages, it is necessary to select the desired photographing condition from those included in the large number of pages. Therefore, the much time is required to select the desired photographing condition. Accordingly, in order to smoothly select the desired photographing conditions, there is a method of reducing the unnecessary photographing conditions, and reducing the number of photographing conditions. However, because the user by himself must determine which photographing condition is necessary, and which photographing condition is unnecessary, it is preferable that the user by himself generates the user own master data.

Accordingly, according to the first embodiment, not the consecutive number but the serial number which is composed of a plurality of classified codes determined in consideration with the characteristic of the radiation diagnosis is attached to each photographing condition. As a result, it is possible to easily perform the editing operation of the photographing conditions, such as the extracting operation, the searching operation, the rearranging operation or the like, by using the classified codes.

More specifically, as shown in FIG. 12, the serial number 23 composed of a plurality of classified codes 22 such as a management flag 22a, a modality 22b, a reserve 22c, first and second body parts 22d and 22e, right and left 22f, a photographing technique 22g, a photographing direction 22h, a branch number 22i or the like, is provide for each photographing condition. Therefore, it is possible to classify the photographing conditions so as to coincide with the characteristic of the radiation diagnosis.

Each of the classified codes 22 will be explained. The management flag 22a comprises a flag for indicating the version of the master code own or distinguishing the original from the copy, or the like. The modality 22b indicates the reading type including the erect, the supine, the cassette and so on. The first body part 22d and the second body part 22e are codes for classifying each photographing condition for every body part (the head, the chest, the abdomen, the neck, the hips, the spine, the lungs, the arm, the leg, or the like). The right and left 22f indicates the type such as a hand, a leg, a jaw, a left (L), a right (R) or the like. The photographing technique 22g is a code for indicating a photographing method such as a simple, a shading, a stress, a forward bending, a backward bending, or the like. The photographing direction 22h is a code for indicating a photographing direction including the AP, the PA, the frontal, the side, the RAO, the LAO, the RL, the LR and so on. The branch number 22i is a code for indicating a print format (1×1, 2×1, 1×2, or the like).

That is, because the conventional photographing conditions are provided with the consecutive numbers respectively, or classified for every body part and provided with numbers, it is impossible to extract or search the photographing conditions according to the detailed photographing condition, or the photographing condition proper to the photographing, such as right and left, the photographing technique, the photographing direction or the like. As a result, it has been difficult to extract the desired photographing conditions from a large quantity of data.

However, according to the present embodiment, because the photographing conditions are classified finely, according to the classified codes proper to the photographing conditions, it is possible to extract and search the photographing conditions variously, and to improve the convenience of the user extremely. Further, because the reserve other than the above-described classified codes is provided, it is possible to classify the photographing conditions according to the conditions proper to the user, and it is possible to meet the case a new photographing condition is added in the future.

The classified codes 22 of the photographing conditions are not limited to the above-described structure. The classified codes 22 may have the structure including at least one classified code indicating the photographing conditions proper to the photographing, reflecting the characteristic of the radiation diagnosis, other than the body part to be photographed.

The method of extracting the photographing conditions required of the user from the master data provided by the maker and generating the user data proper to the user, by using the photographing conditions to each of which the serial number composed of the above-described classified codes 22 is attached, will be explained with reference to the exemplary structures of the screens shown in FIGS. 9 to 11.

FIG. 9 is a view showing an exemplary screen structure of a master editing screen 19 for generating a new master data for the user, by extracting the desired photographing conditions from the original master data or the master data generated by the user. FIG. 10 is a view showing an exemplary screen structure of a condition key editing screen 20 for editing the condition key by reviewing the content or the classification of the user master data generated on the master editing screen 19. FIG. 11 is a view showing an exemplary screen structure of a condition editing screen 21 for displaying and editing the detailed content of each photographing condition.

The editing system for the photographing conditions according to the embodiment, consists of at least the above-described three types of screens.

First, the master editing screen 19 shown in FIG. 9 will be explained. The master editing screen 19 is a screen for generating the photographing condition data (hereinafter, they will be called user master data.) which the user extracts from the original photographing condition data (hereinafter, they will be called maker master data.) provided by the maker. The master editing screen 19 includes an original data display area 19a for displaying the maker master data or the user master data which have been generated, to be copied, and a copy data display area 19b for displaying new user master data to be generated newly. Each of the original data display area 19a and the copy data display area 19b is provided with a scroll function, an extraction function (an extracting condition input area 19c), a search function (a "Search" button 19d), and a rearrangement function (a "Rearrange" button 19e), for displaying the desired photographing conditions.

For example, when the user inputs the chest in the extracting condition input area 19c, the image acquiring display apparatus extracts the desired photographing conditions from the maker master data, on the basis of the chest as the extracting condition. Then, when the photographing condition data are searched so that the first body part 22d of the classified codes 22 is a corresponding value (for example, "1") to the chest, the searched photographing condition is displayed on the original data display area 19a. Herein, according to the structure of the embodiment, because the photographing conditions are classified finely, according to not only the body part (head/neck/chest/abdomen/spine/hips/arm/leg or the like), but also the modality 22b, the right and left 22f, the photographing technique 22g, the photographing direction 22h, the branch 22i or the like, in consideration of the characteristic of the radiation diagnosis, it is possible to extract the desired photographing conditions by using them as the extracting condition. For example, it is possible to extract the photographing conditions which meet the needs of the user, such as photographing conditions used for the specific modality, photographing conditions for photographing according to the specific photographing technique, photographing conditions for photographing in the specific direction, photographing conditions for printing at the specific print format, or the like, according to the classifications inputted as the extracting condition, and further to select the desired photographing conditions easily.

Further, when the user touches the "Rearrange" button 19e, it is possible to rearrange all the photographing condition data in serial number ascending order, serial number descending order, body part ascending order, or body part descending number. Further, when the user touches the "Search" button 19d, it is possible to display the window for the search, and to search the photographing conditions on the basis of the serial number or the name.

Then, when the user makes the display 8d display the desired photographing conditions, by using the scroll function, the extraction function, the search function, or the rearrangement function, the user selects the photographing conditions by clicking with the mouse or moving the cursor, and moves the data from the original data display area 19a to the copy data display area 19b by dragging and dropping the selected photographing conditions. Therefore, the selected photographing conditions are displayed on the copy data display area 19b. Further, when the user touches the "Select All" button 19f, it is possible to specify all the photographing condition data, specify the photographing condition data of the specific body part (head/neck/chest/abdomen/spine/hips/arm/leg or the like), or specify the range of the serial numbers of the photographing conditions. Furthermore, when the user touches the "Copy All" button 19g, it is possible to copy the specified photographing condition data at once. Therefore, it is possible to extract the desired photographing conditions by performing the above-described operations continuously.

When a lot of photographing condition data are copied, it is difficult to distinguish the photographing conditions which have been copied from the photographing conditions which have not been copied. Therefore, the photographing conditions are extracted by selecting the predetermined extracting condition in the extracting condition input area 19c of the copy data display area 19b, rearranged with the "Rearrange" button 19e, or the like. Accordingly, it is possible to confirm the selected photographing conditions. Thereafter, when the user touches the "Copy" button after finishing editing the photographing conditions, the user master data are stored in the storage 8c.

As described above, the original data display are 19a and the copy data display area 19b are contrasted with each other and displayed, and each of them is provided with the scroll function, the extraction function, the search function, and the rearrangement function. Therefore, it is possible to edit the photographing conditions by dragging and dropping them. As a result, it is possible to extract the desired photographing conditions from many photographing conditions easily, and to generate the user master data peculiar to the user.

Further, the operator can review and modify the detailed content of each photographing condition displayed on the original data display area 19a or the copy data display area 19b. In order to review or modify the detailed content of each photographing condition, the operator selects and clicks each section of the photographing conditions. Thereby, the condition editing screen 21 shown in FIG. 11 is displayed. For example, the condition editing screen 21 includes an input condition area 21a and an output condition area 21b. The input condition area 21a is provided with areas displaying the type of the apparatus for reading image data, the primacy condition including the resolution (Low/Standard/High), the pixel size (Standard/Fine) and so on, the read pixel size including the size (8"×10"/10"×12"/11"×14"/14"×17"), the orientation (Portrait/Landscape), the position (Upper/Middle/Lower/Right/Left) and so on, and the read image. The output condition area 21b is provided with areas for determining the type of the printer to which the data are outputted, the print format (1on1/2on1/2on2), the output method (Actual/Part), various types of image enhance, the overlay display and so on. When the operator reviews or edits the detailed contents of the photographing conditions on the condition editing screen 21, the operator starts editing the photographing conditions on the master editing screen 19 again.

As described above, when the user master data are generated and registered by extracting the desired photographing conditions from the maker master data, the photographing conditions of the registered user master data are displayed on the photographing condition selection screen 15. Therefore, because only the necessary and sufficient photographing conditions are displayed on the display, it becomes easy to select the photographing conditions. However, although the number of photographing conditions of the user master data is smaller than the number of those of the maker master data, if the photographing conditions are only listed, it takes long time to select the photographing conditions. Further, some photographing conditions are used individually, and others are combined with each other and used as a set.

For example, usually, there are many cases of photographing the body parts in even-numbered directions, such as frontal and side directions, right and left side directions, right and left oblique directions, or the like, and comparing acquired even-numbered sheets of images with each other. Specifically, regarding the photographing direction of the frontal of the chest or the side of the chest, there are many cases of photographing the chest from the frontal and the side so as to combine two images with each other. Further, in case of photographing the lumbar spine in four directions (the frontal, the side, the right oblique, and the left oblique), it is necessary to adjust the densities of four images. In the case, it is preferable to register a plurality of photographing conditions as a set of photographing conditions.

Therefore, after the user master data are generated, the user classifies the photographing conditions of the user master data for every modality, for every body part to be photographed, or the like, determines the set of photographing conditions, or the like, on the condition key editing screen 20 shown in FIG. 10. The condition key editing screen 20 includes a master data display area 20*a* as well as the copy data display area 19*b* of the master editing screen 19, a modality classifying area 20*b* for selecting the modality, a body part classifying area 20*c* for selecting the body part such as the head, the neck, the chest, the abdomen, the spine, the hips, the arm, the leg or the like, and a condition display area 20*d* on which the photographing conditions of the selected classification are displayed.

When the user specifies the master data on the master specifying input area of the condition key editing screen 20, the specified master data are displayed on the master data display area 20*a*. Then, when the user selects the condition corresponding to any one of the classified codes 22 as the extracting condition on the extracting condition input area, the photographing conditions which meet the selected condition are displayed on the master data display area 20*a*. Thereafter, when the user selects the desired classification in the modality classifying area 20*b* or the body part classifying area 20*c*, the photographing conditions corresponding to the classification are displayed on the condition display area 20*d* with reference to the classified codes 22. The user reviews the contents of the photographing conditions displayed on the condition display area 20*d*. In case the photographing conditions which are displayed automatically with reference to the classified codes 22 are insufficient, it is possible that the user selects the photographing condition individually on the condition display area 20*d* and deletes the selected photographing condition from the classification, or drags and drops the desired photographing condition from the master data display area 20*a* to the condition display area 20*d* and registers it in the classification newly. Further, when the user selects a plurality of photographing conditions on the master data display area 20*a* and moves them to the condition display area 20*b*, it is possible to register the plurality of photographing conditions in the classification as a set condition.

Further, it is possible that the user reviews and edits the detailed content of each photographing condition on the condition key editing screen 20. In order to review and edit the detailed content of each photographing condition, the user clicks each photographing condition on the master data display area 20*a* or the condition display area 20*d*. Thereby, because the condition editing screen 21 is displayed, it is possible to review and edit the detailed content of the photographing condition.

As described above, a new user master data are generated from the maker master data or the user master data which have been generated, the classifications of the new user master data are modified, or the set of photographing conditions is registered in the new user master data, on the master editing screen 19, the condition key editing screen 20 or the condition editing screen 21. Thereby, the photographing conditions classified so as to reflect the content of the user master data are displayed on the classified condition display area 15*b* of the photographing condition selection screen 15. As a result, it is possible to improve the convenience of the user.

According to the editing system for the photographing conditions or the method for editing the photographing conditions of the above-described embodiment, because the serial number consisting a plurality of classified codes determined in consideration of the characteristic of the radiation diagnosis is attached to the photographing condition, it is possible to extract or search the photographing condition more highly and variously than the conventional. Further, because the editing screens shown in FIGS. 9 to 11 are provided, it is possible that the user who is inexperienced in the mechanical operation extracts the desired photographing conditions from a large number of photographing conditions, modifies the classifications of the photographing conditions, or registers a plurality of photographing conditions as a set of photographing conditions.

Second Embodiment

Next, the image acquiring display apparatus comprising the editing system for the photographing conditions, the method for editing the photographing conditions by using the apparatus, and a program for arranging the photographing conditions, according to the second embodiment of the present invention, will be explained with reference to FIGS. 13 and 14.

Figure 13:
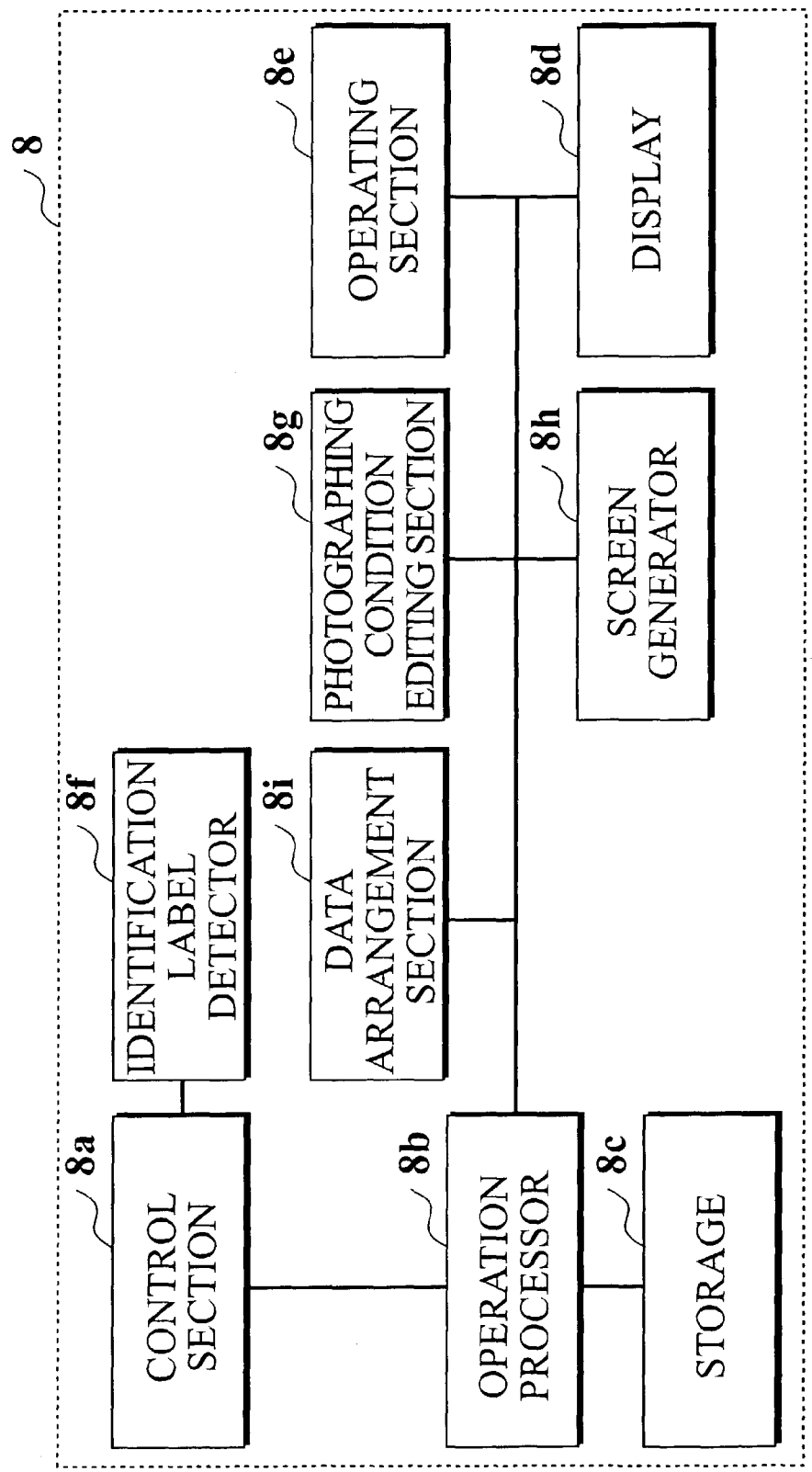
FIG. 13 is a block diagram showing the structure of the controller 8 composing the radiographic image diagnostic system 1, according to a second embodiment of the present invention.

FIG. 13 is a block diagram showing the structure of the controller 8 comprising the editing system for the photographing conditions according to the second embodiment. FIG. 14 is a view showing the structure of the classified codes 22 attached to each photographing condition. The second embodiment is characterized by the learning function provided for the photographing condition editing section 8*g* and the order of displaying photographing conditions, which is rearranged automatically. The structure and the operation of another part are the same as the first embodiment.

That is, according to the above-described first embodiment, the user generates the user master data by using the master editing screen 19, the condition key editing screen 20, the condition editing screen 21 or the like, by himself. However, some photographing conditions become used frequently, and others photographing conditions become hardly used, as the user photographs continuously, regardless of the user master data generated by the user. In the case, when the user deletes the unnecessary photographing conditions on the editing screens, it is possible to make the photographing condition selection screen 15 used easily. However, it is possible that the controller 8 adjusts the structure or the displaying order of the photographing conditions automatically, with reference to the frequencies of selecting the photographing conditions.

For example, as shown in FIG. 13, the controller 8 is provided with the controller 8a, the operation processor 8b, the storage 8c, the display 8d, the operating section 8e, the identification label detector 8f, the photographing condition editing section 8g, and the screen generator 8h, and further a data arrangement section 8i for rearranging the user master data with reference to the frequency of selecting each photographing section. Therefore, it is possible to renew the displaying order of the photographing conditions according to the frequency of selecting each photographing condition, as the occasion may demand, when generating the photographing condition selection screen 15.

Figure 14:
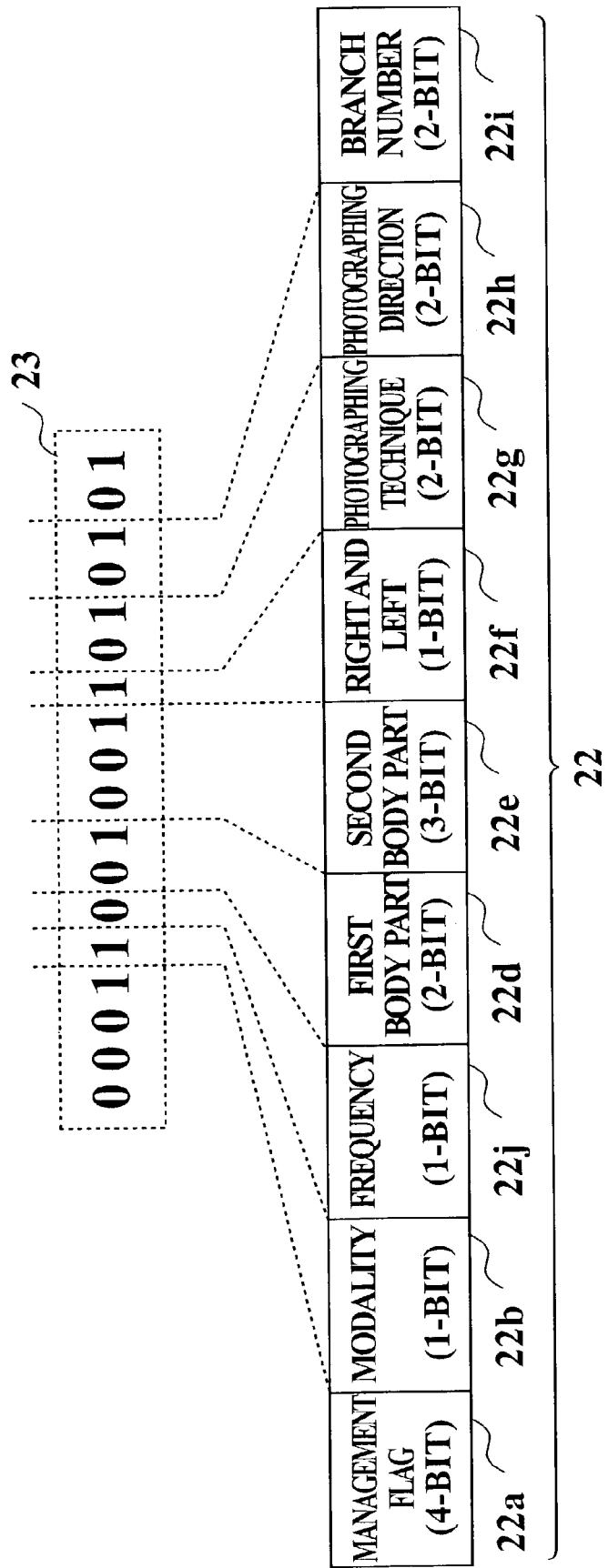
FIG. 14 is a view showing the structure of classified codes 22 attached to each of photographing conditions, according to the second embodiment.

In order to realize the rearrangement of the photographing conditions, for example, as shown in FIG. 14, a frequency area 22j in which the numeral value corresponding to the frequency of selecting each photographing condition is written, is provided for the reserve area of the classified codes 22 attached to each photographing condition. Thereby, when the photographing condition is selected on the photographing condition selection screen 15, the storage 8c stores the frequency of selecting the photographing condition, which is added in order, and the operation processor 8b writes the frequency of selecting the photographing condition or the corresponding value to the frequency in the frequency area 22j. Thereby, it is possible to distinguish the photographing conditions from each other. Further, because some photographing conditions which are selected frequently, are displayed at the previous positions, and others which are hardly selected, are displayed at the next positions, according to the frequency of selecting each photographing condition, it is possible to reduce the time the user selects the desired photographing condition.

Further, the date of selecting each photographing condition, instead of the frequency of selecting the photographing condition, may be stored in a predetermined area of the classified codes 22. Thereby, it is possible to display the photographing conditions in new order of the date. Further, it is possible to display the body part which is frequently required to be photographed in an emergency, at the previous position, or to display the body part which is related to a plurality of doctors, radiologists or departments, at the previous position. In the case, the maker or the user may enters the numeral value in a predetermined area of the classified codes 22 of each photographing condition. Then, the order of displaying the photographing conditions may be determined with reference to the numeral value of each photographing condition when generating the photographing condition selection screen 15.

The above-described rearrangement of the order of displaying the photographing conditions can be performed automatically. In order to attain it, a program for arranging the photographing conditions is loaded in and executed by the controller 8, the program for performing a processing of extracting the value of the predetermined classified code 22 from the serial number 23 of each photographing condition, a processing of adding the value of the predetermined code 22 of the photographing condition selected on the photographing condition selection screen 15, a processing of ordering a plurality of photographing conditions with reference to the predetermined classified codes 22, and a processing of determining the position of each photographing condition on the basis of the order.

As described above, displaying the characteristics of the serial number consisting of a plurality of classified codes, because the frequency of selecting each photographing condition, the photographing data on each photographing condition, or the like is written in the classified code, and the order of displaying the photographing conditions is renewed automatically, in consideration of the values of the classified codes, it is possible to always display the screen which the user can use easily, reduce the time the user selects the desired photographing conditions, and diagnose the medical image smoothly.

According to the above-described embodiment, it have been explained to edit the photographing conditions. However, the present invention is not limited to the above-described embodiment. The present invention can be applied to an editing system, an editing method and an editing apparatus, for extracting suitable data for the state used by the user from an arbitrary data sequence, and generating a new data sequence.

As described above, according to the image acquiring display apparatus comprising the editing system for photographing conditions, of the present invention, the method for editing photographing conditions by using the apparatus, and the program for arranging photographing conditions, the following effects will be indicated.

A first effect of the present invention is that a user can edit user master data easily and certainly, by himself.

The reason is that photographing conditions can be extracted or searched by using not only the body part but also the photographing technique, the photographing direction or the like, because the serial number comprising a plurality of classified codes determined in consideration of the characteristic of the radiation diagnosis, is attached to each of the photographing conditions. Further, desired photographing conditions can be displayed and edited by being dragged and dropped, because the master editing screen for generating the user master data from the maker master data, the condition key editing screen for reviewing or editing the classification of the user master data, or the condition editing screen for reviewing or editing each of the photographing conditions, is used as the editing screen, and each editing screen is provided with the extraction function, the search function and the rearrangement function.

A second effect of the present invention is that the order of displaying the photographing conditions is automatically renewed according to the frequency of selecting each of the photographing conditions.

The reason is that the controller can perform the processing of extracting the value of the predetermined classified code of each photographing condition, the processing of rewriting the value of the classified code of the photographing condition selected, the processing of determining the order of displaying the photographing conditions on the basis of the value of the classified code of each photographing condition, and the processing of determining the position of displaying each photographing condition on the basis of the order, because the program for arranging photographing conditions is loaded in the controller comprising the editing system.

According to the above-described effects, it is possible that the user always selects the desired photographing conditions on the screen which the user can use easily. As a result, it is possible to diagnose the medical image smoothly.

The entire disclosure of Japanese Patent Application No. Tokugan 2002-18404 filed on Jan. 28, 2002 including specification, claims, drawings and summary are incorporated herein by reference in its entirety.

What is claimed is:

1. An image acquiring display apparatus comprising:
a display for displaying at least a selection screen for selecting a photographing condition required for a patient from a plurality of photographing conditions, and a display screen for displaying image data read out of a radiographic image conversion medium having a radiographic image of the patient, recorded thereon; and
an editing section for editing a plurality of photographing conditions to be displayed on the selection screen, of predetermined master data including a plurality of photographing conditions, wherein
a serial number is attached to each of the plurality of photographing conditions included in the master data, the serial number comprising a plurality of classified codes classifiable of each of the plurality of photographing conditions,
a combination of at least two selected of at least a body part to be photographed, a modality, a photographing technique, a photographing direction and a print format, is used as the plurality of classified codes,
the editing section generates a first editing screen for extracting a plurality of photographing conditions required for a user, from the plurality of photographing conditions included in the master data, and generating user data peculiar to the user, a second editing screen for modifying or editing a classification of the user data generated, and a third editing screen for modifying or editing each of the plurality of photographing conditions included in the user data, and changes the first editing screen, the second editing screen and the third editing screen, with switches provided for the first editing screen, the second editing screen and the third editing screen, respectively,
an original data display area on which the master data or the user data generated are displayed and a copy data display area on which the user data to be generated are displayed, are contrasted with each other and formed on the first editing screen,
each of the original data display area and the copy data display area is provided with an extracting section for extracting the photographing conditions on the basis of each of the classified codes, a searching section for searching the photographing conditions by using the serial number or the photographing conditions, and a rearranging section for rearranging the photographing conditions by using the serial number or the body part of each of the photographing conditions, and
the user data are generated by dragging, moving and dropping a predetermined photographing condition from the original data display area to the copy data display area.

2. The apparatus as claimed in claim 1, wherein an input condition area on which a type of an apparatus for reading the image data, a reading condition and a read Image are displayed, and an output condition area on which a type of an apparatus for outputting the image data, an output condition, an image processing condition and an output image are displayed, are formed on the third editing screen, and a photographing condition selected, is edited on the input condition area or the output condition area.

3. The apparatus as claimed in claim 1, further comprising:
an extracting section for extracting a predetermined classified code from the plurality of classified codes of the serial number, with reference to the serial number;
a code determining section for determining a value of the predetermined classified code of each of the plurality of photographing conditions to be displayed on the selection screen, according to a frequency or a date of selecting each of the plurality of photographing conditions;
an order determining section for determining an order of displaying the plurality of photographing conditions, with reference to the value of the predetermined classified code of each of the plurality of photographing conditions; and
a position determining section for determining a position of displaying each of the plurality of photographing conditions on the selection screen, on the basis of the order.

4. An image acquiring display apparatus comprising:
a display for displaying at least a selection screen for selecting a photographing condition required for a patient from a plurality of photographing conditions, and a display screen for displaying image data read out of a radiographic image conversion medium having a radiographic image of the patient, recorded thereon; and
an editing section for editing a plurality of photographing conditions to be displayed on the selection screen, of predetermined master data including a plurality of photographing conditions, wherein
a serial number is attached to each of the plurality of photographing conditions included in the master data, the serial number comprising a plurality of classified codes classifiable of each of the plurality of photographing conditions,
a combination of at least two selected of at least a body part to be photographed, a modality, a photographing technique, a photographing direction and a print format, is used as the plurality of classified codes,
the editing section generates a first editing screen for extracting a plurality of photographing conditions required for a user, from the plurality of photographing conditions included in the master data, and generating user data peculiar to the user, a second editing screen for modifying or editing a classification of the user data generated, and a third editing screen for modifying or editing each of the plurality of photographing conditions included in the user data, and changes the first editing screen, the second editing screen and the third editing screen, with switches provided for the first editing screen, the second editing screen and the third editing screen, respectively,
a data display area on which the user data to be generated are displayed, a modality classifying area for specifying the modality of each of the photographing conditions, a body part classifying area for specifying the body part of each of the photographing conditions, and an individual display area on which a photographing condition to which the serial number comprising classified codes of the modality specified and the body part specified is attached, is displayed, are formed on the second editing screen,
the data display area is provided with an extracting section for extracting the photographing conditions on the basis of each of the classified codes, and a searching section for searching the photographing conditions by using the serial number or the photographing conditions, and the classification of the user data is modified by dragging, moving and dropping a predetermined photographing condition from the data display area to the individual display area.

5. The apparatus as claimed in claim 4, wherein a plurality of photographing conditions selected on the data display area are moved to the individual display area, together, and registered in the user data, as a set of conditions.

6. The apparatus as claimed in claim 4, wherein an input condition area on which a type of an apparatus for reading the image data, a reading condition and a read image are displayed, and an output condition area on which a type of an apparatus for outputting the image data, an output condition, an image processing condition and an output image are displayed, are formed on the third editing screen, and a photographing condition selected, is edited on the input condition area or the output condition area.

7. The apparatus as claimed in claim 4, further comprising:
an extracting section for extracting a predetermined classified code from the plurality of classified codes of the serial number, with reference to the serial number;
a code determining section for determining a value of the predetermined classified code of each of the plurality of photographing conditions to be displayed on the selection screen, according to a frequency or a date of selecting each of the plurality of photographing conditions;
an order determining section for determining an order of displaying the plurality of photographing conditions, with reference to the value of the predetermined classified code of each of the plurality of photographing conditions; and
a position determining section for determining a position of displaying each of the plurality of photographing conditions on the selection screen, on the basis of the order.

8. A method for editing photographing conditions, comprising:
displaying an editing screen for editing a plurality of photographing conditions required for a user, of predetermined master data including a plurality of photographing conditions required for a patient;
editing the plurality of photographing conditions required for the user, of the predetermined master data, on the editing screen;
attaching a serial number comprising a plurality of classified codes classifiable of each of the plurality of photographing conditions included in the master data, according to a characteristic of each of the plurality of photographing conditions, to each of the plurality of photographing conditions;
classifying each of the plurality of photographing conditions according to the serial number;
using a combination of at least two selected of at least a body part to be photographed, a modality, a photographing technique, a photographing direction and a print format, as the plurality of classified codes;
generating a first editing screen for extracting a plurality of photographing conditions required for the user, from the plurality of photographing conditions included in the master data, and generating user data peculiar to the user, a second editing screen for modifying or editing a classification of the user data generated, and a third editing screen for modifying or editing each of the plurality of photographing conditions included in the user data;
changing the first editing screen, the second editing screen and the third editing screen, with switches provided for the first editing screen, the second editing screen and the third editing screen, respectively;
displaying an original data display area on which the master data or the user data generated are displayed and a copy data display area on which the user data to be generated are displayed, so as to be contrasted with each other, on the first editing screen;
providing an extracting section for extracting the photographing conditions on the basis of each of the classified codes, a searching section for searching the photographing conditions by using the serial number or the photographing conditions, and a rearranging section for rearranging the photographing conditions by using the serial number or the body part of each of the photographing conditions, for each of the original data display area and the copy data display area; and
generating the user data by dragging, moving and dropping a predetermined photographing condition from the original data display area to the copy data display area.

9. The method as claimed in claim 8, further comprising:
displaying an input condition area on which a type of an apparatus for reading the image data, a reading condition and a read image are displayed, and an output condition area on which a type of an apparatus for outputting the image data, an output condition, an image processing condition and an output image are displayed, on the third editing screen; and
editing a photographing condition selected, on the input condition area or the output condition area.

10. A method for editing photographing conditions, comprising:
displaying an editing screen for editing a plurality of photographing conditions required for a user, of predetermined master data including a plurality of photographing conditions required for a patient;
editing the plurality of photographing conditions required for the user, of the predetermined master data, on the editing screen;
attaching a serial number comprising a plurality of classified codes classifiable of each of the plurality of photographing conditions included in the master data, according to a characteristic of each of the plurality of photographing conditions, to each of the plurality of photographing conditions;
classifying each of the plurality of photographing conditions according to the serial number;
using a combination of at least two selected of at least a body part to be photographed, a modality, a photographing technique, a photographing direction and a print format, as the plurality of classified codes;
generating a first editing screen for extracting a plurality of photographing conditions required for the user, from the plurality of photographing conditions included in the master data, and generating user data peculiar to the user, a second editing screen for modifying or editing a classification of the user data generated, and a third editing screen for modifying or editing each of the plurality of photographing conditions included in the user data;
changing the first editing screen, the second editing screen and the third editing screen, with switches provided for the first editing screen, the second editing screen and the third editing screen respectively;
displaying a data display area on which the user data to be generated are displayed, a modality classifying area for specifying the modality of each of the photographing conditions, a body part classifying area for specifying the body part of each of the photographing conditions, and an individual display area on which a photographing condition to which the serial number comprising classified codes of the modality specified and the body part specified is attached, is displayed, on the second editing screen;

providing an extracting section for extracting the photographing conditions on the basis of each of the classified codes, and a searching section for searching the photographing conditions by using the serial number or the photographing conditions, for the data display area; and modifying the classification of the user data by dragging, moving and dropping a predetermined photographing condition from the data display area to the individual display area.

11. The method as claimed in claim 10, further comprising: moving a plurality of photographing conditions selected on the data display area to the individual display area, together, and registering them in the user data, as a set of conditions.

12. The method as claimed in claim 10, further comprising:

displaying an input condition area on which a type of an apparatus for reading the image data, a reading condition and a read image are displayed, and an output condition area on which a type of an apparatus for outputting the image data, an output condition, an image processing condition and an output image are displayed, on the third editing screen; and editing a photographing condition selected, on the input condition area or the output condition area.

13. An image acquiring display apparatus comprising:

a display for displaying at least a selection screen for selecting a photographing condition required for a patient from a plurality of photographing conditions, and a display screen for displaying image data read out of a radiographic image conversion medium having a radiographic image of the patient, recorded thereon; and an editing section for editing a plurality of photographing conditions to be displayed on the selection screen, of predetermined master data including a plurality of photographing conditions, wherein a serial number is attached to each of the plurality of photographing conditions included in the master data, the serial number comprising a plurality of classified codes classifiable of each of the plurality of photographing conditions, the apparatus further comprising:

an extracting section for extracting a predetermined classified code from the plurality of classified codes of the serial number, with reference to the serial number;

a code determining section for determining a value of the predetermined classified code of each of the plurality of photographing conditions to be displayed on the selection screen, according to a frequency or a date of selecting each of the plurality of photographing conditions;

an order determining section for determining an order of displaying the plurality of photographing conditions, with reference to the value of the predetermined classified code of each of the plurality of photographing conditions; and a position determining section for determining a position of displaying each of the plurality of photographing conditions on the selection screen, on the basis of the order.

\* \* \* \* \*